United States Patent [19]

Law et al.

[11] Patent Number: 6,040,496

[45] Date of Patent: Mar. 21, 2000

[54] USE OF TRANSLATIONALLY ALTERED RNA TO CONFER RESISTANCE TO MAIZE DWARF MOSAIC VIRUS AND OTHER MONOCOTYLEDONOUS PLANT VIRUSES

[75] Inventors: Marcus Dixon Law, Chapel Hill; Jon M. Dietz, Apex, both of N.C.

[73] Assignee: Novartis Finance Corporation, New York, N.Y.

[21] Appl. No.: 08/496,944

[22] Filed: Jun. 30, 1995

[51] Int. Cl.⁷ .............................. A01H 5/00; C12N 5/04; C12N 15/82
[52] U.S. Cl. ..................... 800/280; 800/301; 536/23.72; 435/468
[58] Field of Search .................................. 800/205, 279, 800/301, 280; 536/23.1, 23.72; 435/172.3, 240.4, 320.1, 69.1, 419, 418, 468

[56] References Cited

U.S. PATENT DOCUMENTS

| | | | |
|---|---|---|---|
| 5,034,323 | 7/1991 | Jorgensen et al. | 435/172.3 |
| 5,283,184 | 2/1994 | Jorgensen et al. | 435/172.3 |
| 5,428,144 | 6/1995 | Blair et al. | 536/23.72 |

FOREIGN PATENT DOCUMENTS

| | | |
|---|---|---|
| 0342926A2 | 5/1989 | European Pat. Off. . |
| 0578627A1 | 7/1993 | European Pat. Off. . |
| 91/13542 | 9/1991 | WIPO . |
| WO 93/14210 | 7/1993 | WIPO . |
| 93/17098 | 9/1993 | WIPO . |
| 94/18336 | 8/1994 | WIPO . |
| 94/21796 | 9/1994 | WIPO . |
| WO 95/04825 | 2/1995 | WIPO . |
| 95/09920 | 4/1995 | WIPO . |

OTHER PUBLICATIONS

Smith, Holly A., "Transgenic Plant Virus Resistance Mediated by Untranslatable Sense RNAs: Expression, Regulation, and Fate of Nonessential RNAs", *The Plant Cell*, 6: 1441–1453 (1994).

Bazan et al., "Viral cysteine proteases are homologous to the trypsin–like family of serine proteases: Structural and functional implications", *Proc. Natl. Acad. Sci. USA*, 85: 7872–7876 (1988).

Chasan, R., "Making Sense (Suppression) of Viral RNA–Mediated Resistance", *The Plant Cell*, 6: 1329–1331 (1994).

de Haan et al., "Characterization of RNA–Mediated Resistance to Tomato Spotted Wilt Virus in Transgenic Tobacco Plants", *Bio/Technology*, 10:1133–1337 (1992).

Domier, et al., "Potyviral Proteins Share Amino Acid Sequence Homology with Picorna–, Como–, and Cauli-moviral Proteins", *Virology*, 158: 20–27 (1987).

Dougherty et al., "Expression and Function of Potyviral Gene Products", *Ann. Rev. Phytopathol.*, 26: 123–143 (1988).

Dougherty et al., "RNA–Mediated Virus Resistance in Transgenic Plants" Exploitation of a Cellular Pathway Possibly Involved in RNA Degradation, *Molecular Plant–Microbe Interactions* 7(5):544–552 (1994).

Fang et al., "Genetic Engineering of Potyvirus Resistance Using Constructs Derived from the Zucchini Yellow Mosiac Virus Coat Protein Gene", *Molecular Plant–Microbe Interactions*, 6(3) 358–367 (1993).

Fitchen et al., "Genetically Engineered Protection Against Viruses in Transgenic Plants", *Ann. Rev. Microbiol.*, 47:739–763 (1993).

Frenkel et al., "Unexpected sequence diversity in the amino–terminal ends of the coat proteins of strains of sugarcane mosiac virus", *J. Gen. Virol.*, 72: 237–242 (1991).

Gorbalenya et al., "Two related superfamilies of putative helicases involved in replication, recombination, repair and expression of DNA and RNA genomes", *Nucleic Acids Research*, 17(12): 4713–4730 (1989).

Gough et al., "Nucleotide Sequence of the Capsid and Nuclear Inclusion Protein Genes from the Johnson Grass Strain of Sugarcane Mosiac Virus RNA", *J. Gen. Virol.*, 68: 297–304 (1987).

Huiet et al., "Nucleotide sequence and RNA hybridization analyses reveal an ambisense coding strategy for maize stripe virus RNA3", *Virology*, 182: 47–53 (1991).

Huiet et al., "Complete sequence of maize stripe virus RNA4 and mapping of its subgenomic RNAs", *J. Gen. Virol.*, 73: 1603–1607 (1992).

Knoke et al., "Maize Dwarf Mosaic, Maize Chlorotic Dwarf, and Maize Streak", *Plant Diseases of International Importance*, I: 235–281, Prentice Hall (1992).

Lindbo et al., "Pathogen–Derived Resistance to a Potyvirus: Immune and Resistant Phenotypes in Transgenic Tobacco Expressing Altered Forms of a Potyvirus Coat Protein Nucleotide Sequence", *Molecular Plant–Microbe Interactions*, 5(2): 144–153 (1992).

Lindbo et al., "Untranslatable Transcripts of the Tobacco Etch Virus Coat Protein Gene Sequence Can Interfere with Tobacco Etch Virus Replication in Transgenic Plants and Protoplastss", *Virology*, 189: 725–733 (1992).

Lindbo et al., "Induction of a Highly Specifc Antiviral State in Transgenic Plants: Implications for Regulation of Gene Expression and Virus Resistance", *The Plant Cell* 5: 1749–1759 (1993).

(List continued on next page.)

*Primary Examiner*—Elizabeth F. McElwain
*Attorney, Agent, or Firm*—Mary Kymne Hehman; Thomas Hoxie

[57] ABSTRACT

The present invention provides methods and compositions for inhibiting virus infection in susceptible monocotyledonous plants. The methods and compositions involve the production of translationally altered forms of messenger RNA sequence derived from the inhibited virus. The invention further provides structural and organizational information for the genome of strain B of maize dwarf mosaic virus. Methods for inhibiting MDMV-B infection are taught. These methods include the generation of transformed plants containing chimeric genes capable of expressing either MDMV-B proteins or translationally altered forms of messenger RNA sequences produced by MDMV-B.

15 Claims, No Drawings

OTHER PUBLICATIONS

Marzachi et al., "Cloning of the Maize Rough Dwarf Virus Genome: Molecular Confirmation of the Plant–Reovirus Classification Scheme and Identification of Two Large Non-overlapping Coding Domains within a Single Genomic Segment", *Virology,* 180: 518–526 (1991).

Mirkov et al., "Engineering Sugarcane for Resistance to Sugarcane Mosaic Virus", Abstract P29–4, 1995 ASV Meeting, p. 178.

Morch et al., "A new 'sense' RNA approach to block viral RNA replication in vitro", *Nucleic Acids Research,* 15(10) 4123–4130 (1987).

Mullineaux et al., "The nucleotide sequence of maize streak virus DNA", *EMBO J.,* 3: 3063–3068 (1984).

Murry et al., "Transgenic Corn Plants Expressing MDMV Strain B Coat Protein are Resistant to Mixed Infections of Maize Dwarf Mosaic Virus and Maize Chlorotic Mottle Virus", *Bio/Technology,* 11: 1559–1564 (1993).

Nutter et al., "The complete nucleotide sequence of the maize chlorotic mottle virus genome", *Nucleic Acids Research,* 17: 3163–3177 (1989).

Oh et al., "Identification of Essential Residues in Potyvirus Proteinase HC–Pro by Site–Directed Mutagenesis", *Virology,* 173: 692–699 (1989).

Pang et al., "Different Mechanisms Protect Transgenic Tobacco Against Tomato Spotted Wilt and Impatiens Necrotic Spot Tospoviruses", *Bio/Technology,* 11: 819–824 (1993).

Poch et al., "Identification of four conserved motifs among the RNA–dependent polymerase encoding elements", *EMBO,* 8: 3867–3874 (1989).

Powell et al., "Protection against Tobacco Mosaic Virus Infection in Transgenic Plants Requires Accumulation of Coat Protein Rather than Coat Protein RNA Sequences", *Virology* 175: 124–130 (1990).

Riechmann et al., "Highlights and prospects of potyvirus molecular biology", *Journal of General Virology,* 73: 1–16 (1992).

Sohn et al., "Sequence analysis of the 3'–terminal half of RNA 1 of wheat spindle streak mosaic virus", *Arch. Virol.,* 135: 279–292 (1994).

Van der Wilk et al., "Expression of the potato leafroll luteovirus coat protein gene in transgenic potato plants inhibits viral infection", *Plant Mol. Biol.,* 17: 431–439 (1991).

Vardi et al., "Plants transformed with a cistron of a potato virus Y protease (Nia) are resistant to virus infection", *Proc. Natl. Acad. Sci.,* 90: 7513–7517 (1993).

Vincent et al., "Nucleotide Sequence analysis and genomic organization of the NY–RPV isolate of barley yellow dwarf virus", *J. Gen. Virol.,* 72: 2347–2355 (1991).

Wilson et al., "Plant Viruses: A Tool–Box for Genetic Engineering and Crop Protection", *BioEssays,* 10(6): 179–186 (1989).

USE OF TRANSLATIONALLY ALTERED RNA TO CONFER RESISTANCE TO MAIZE DWARF MOSAIC VIRUS AND OTHER MONOCOTYLEDONOUS PLANT VIRUSES

FIELD OF THE INVENTION

The invention relates generally to the genetic engineering of monocotyledonous plants to resist virus infection through the expression of inhibitory transcripts or proteins derived from the inhibited virus. In another aspect, the invention relates to the elucidation and characterization of the genomic structure and organization of a maize dwarf mosaic virus.

BACKGROUND OF THE INVENTION

Genetically Engineering Plants for Virus Resistance

Plant viruses are a major problem in agriculture and cause significant losses in crop yield each year. In the past, available approaches for combating plant viruses were primarily limited to the selection of plant lines which exhibited genetic resistance to virus infection and the application of chemicals designed to protect plants from the organisms responsible for introducing the virus to the plant (i.e. viral vectors).

Recently, a number of approaches for combating plant viruses have been developed which are based upon the transformation of susceptible plant species with chimeric genes which express transcripts or proteins that inhibit viral infection. These approaches include genetically engineering plants to express viral coat protein or coat protein transcripts, viral replicases in unmodified or modified form, antisense genes or ribozymes targeting viral genomnic RNA or transcripts, and altered viral transcripts (for a review, see Fitchen, J. H. et al., *Ann. Rev. Microbiol.* 47. 739–763 (1993)). To apply any of these approaches, knowledge of the structure and organization of the genome of the target virus is necessary.

With respect to the expression of altered viral transcripts to confer viral resistance, limited success has been reported in dicotyledonous plants through the expression of viral coat protein transcripts which have been modified to render them incapable of translation. Expression of such "untranslatable" viral transcripts in tobacco has been reported to inhibit tobacco etch virus (Lindbo, J. A. et al., *Mol. Plant-Microbe Int.* 5(2): 144–153 (1992); Lindbo, J. A. et al., *Virology* 189: 725–733 (1992); PCT application publication no. WO 93/17098 to Dougherty, W. G. et al. (Sep. 2, 1993); Lindbo, J. A. et al., *The Plant Cell* 5: 1749–1759 (1993)), tomato spotted wilt virus (Pang, S. et al., *Biotechnology* 11: 819–824 (1993); DeHaan et ai, *Bio/Technology* 10: 1133–1137 (1992) and potato virus Y (Van der Vlugt, R. A. et al., *Plant Mol. Biol.* 17: 431–439 (1991).

The ability of such untranslatable RNAs to inhibit viral infection does not appear to be universal, however. Failure of such altered viral transcripts to inhibit viral infection have been reported for tobacco mosaic virus (Powell, P. A. et al., *Virology* 175: 124–130 (1990) and zucchini yellow mosaic virus (Fang, G. et al., *Mol. Plant-Microbe Int.* 6(3): 358–367 (1993), a potyvirus similar to tobacco etch virus. Additional unreported failures may also exist, since such negative results are rarely published.

Maize Dwarf Mosaic Virus

Maize dwarf mosaic virus (MDMV) is classified as a member of a group of plant viruses known as the potyviruses. The potyviruses are the largest group of plant viruses and are characterized by a long, flexuous rod particle morphology and are non-persistently transmitted by aphid vectors (see Hollings, M. and Brunt, A., pages 732–807 of "Handbook of Plant Virus Infection and Comparative Diagnosis", ed. by E. Kurstak, pub. by Elsevier/North Holland Biomedical Press, Amsterdam (1981)). The potyviruses have a genome composed of a single strand positive sense messenger RNA molecule which is transcribed and translated as one polyprotein that is subsequently cleaved into its component parts.

MDMV is a major crop pest in maize where it causes mosaic symptoms and dwarfing of infecting plants, ultimately reducing crop yields (Knoke, J. K. et al., pages 235–281 of "Diseases of Cereals & Pulses", volume I, ed. by Singh, U.S. et al., pub. by Prentice Hall, Englewood Cliffs, N.J. (1992)). When found in combination with maize chlorotic mottle virus (MCMV), a synergistic condition known as corn lethal necrosis results causing even more severe crop damage (see Uyemoto, J. K., pages 141–143 of "Proc. Int'l. Maize Virus Disease Colloq. & Workshop", ed. by Gordon, D. T. et al., pub. by Ohio State Univ. and Ohio Agric. Res. Dev. Center, Wooster, Mass. (1983).

The economic impact of yield losses due to MDMV has generated considerable interest in developing strategies to combat this virus. To date, however, only limited success has been achieved in reducing the adverse impact of this virus. Thus there remains a need to identify additional effective means for protecting host plants from MDMV.

The genomic structure and organization of MDMV has remained largely uncharacterized except for the elucidation of viral coat protein coding sequences (see Frenkel, M. J. et al. *J. Gen. Virol.* 72:237–242, (1991); see also Murray, L. E. et al., *Bio/Technology* 11: 1559–1564 (1993)). As a result, it is currently not possible to apply many of the more recent recombinant-DNA based approaches that have been used for combating plant viruses to MDMV. These approaches require a more extensive understanding of the structure and organization of the genome of the target virus than is currently available for MDMV.

SUMMARY OF THE INVENTION

In one aspect, the present invention provides a method for protecting a monocotyledonous plant from infection by a virus by producing in such a plant an RNA molecule whose sequence corresponds, at least in part, to a mRNA or the plus strand RNA produced by the virus. The RNA molecule produced according to the method of the invention is modified so that it cannot be translated completely as compared to the viral RNA to which it corresponds. Included within this aspect of the invention are chimeric genes designed to express such modified RNA molecules in monocotyledonous plants, as well as monocotyledonous plants containing such chimeric genes stably integrated into their genome. Such plants and their progeny are protected from infection by monocotyledonous viruses that produce messenger or plus-sense RNA which share sequence identity with the modified RNA molecule encoded and expressed by the stably integrated chimeric gene.

Another aspect of the invention is based upon structural and organizational information that has been elucidated for the genome of strain B of Maize Dwarf Mosaic Virus (MDMV-B) upstream of the coat protein gene. Included in this aspect of the invention are chimeric genes designed to express coding sequences for MDMV-B proteins including the coat protein (nucleotides 7308–8291 of SEQ ID No. 1), the RNA dependent RNA polymerase (RdRp) (nucleotides 5745–7307 of SEQ ID No. 1), proteinase (nucleotides 4452–5744 of SEQ ID No. 1), a 6K protein (nucleotides 4293–4451 of SEQ ID No. 1), cylindrical inclusion protein (CIP) (nucleotides 2376–4292 of SEQ ID No. 1), P3 proteinase (nucleotides 1134–2375 of SEQ ID No. 1), and a portion of the helper component-P2 proteinase (HC-Pro) (nucleotides 3–1133 of SEQ ID No. 1). Methods for protecting plants from MDMV infection by transforming them with these chimeric genes are included within this aspect of the invention along with the resulting transgenic plants and their progeny.

The MDMV-B coding sequences may also be modified according to the first aspect of the present invention so that the RNA derived therefrom cannot be properly translated. The present invention includes chimeric genes designed to express such translationally altered MDMV-B RNAs in plants. Methods for protecting plants from MDMV infection by transforming them with these chimeric genes are included within this aspect of the invention along with the resulting transgenic plants and their progeny.

DESCRIPTION OF THE SEQUENCE LISTING

SEQ ID No. 1: Sequence of the polycistronic messenger RNA of maize dwarf mosaic virus, strain B. Various features of this sequence are described under item II of the "Detailed Description of the Invention".

SEQ ID NO. 2: Sequence of the polyprotein encoded by the polycistronic messenger RNA of maize dwarf mosaic virus, strain B. Various features of this polyprotein are described under item II of the "Detailed Description of the Invention".

SEQ ID No. 3: First internal control alcohol dehydrogenase PCR primer used in analysis of $T_0$ plants as described in Example 4.

SEQ ID No. 4: Second internal control alcohol dehydrogenase PCR primer used in analysis of $T_0$ plants as described in Example 4.

SEQ ID No. 5: First PCR primer for the synthetic PAT gene used in analysis of $T_0$ plants as described in Example 4.

SEQ ID No. 6: Second PCR primer for the synthetic PAT gene used in analysis of $T_0$ plants as described in Example 4.

SEQ ID No. 7: First PCR primer for the NIa proteinase gene used in analysis of $T_0$ plants as described in Example 4.

SEQ ID No. 8: Second PCR primer for the NIa proteinase gene used in analysis of $T_0$ plants as described in Example 4.

DEFINITIONS

For purposes of describing the present invention, the term "translationally altered RNA" is used to refer to a modified form of a naturally occurring messenger RNA sequence which cannot be completely translated compared to the unmodified, naturally occurring form. A translationally altered RNA may be incapable of being translated at all or it may be capable of being partially translated into an attenuated peptide corresponding to a portion of the peptide encoded by the naturally occurring messenger RNA sequence from which the translationally altered RNA is derived.

The coding sequence for a naturally occurring viral RNA sequence may be modified to encode a translationally altered RNA, for example, by removing its ATG initiation codon or by utilizing a portion which does not include the initiation codon. Other means for translationally altering a naturally occurring viral RNA molecule include introducing one or more premature stop codons and/or interrupting the reading frame.

DETAILED DESCRIPTION OF THE INVENTION

The basis for the present invention is two-fold. The first basis for the present invention is the discovery that reduced susceptibility to infection by a virus may be conferred upon a monocotyledonous plant by producing in the plant a translationally altered RNA molecule corresponding in sequence to a plus-sense or messenger RNA molecule of the target virus. The second basis for the present invention is the elucidation and characterization by the inventors of the genomic structure and organization of strain B of maize dwarf mosaic virus (MDMV-B). These two bases are addressed consecutively below and are both represented by the examples demonstrating resistance to MDMV-B via expression of a translationally altered RNA in a transgenic maize plant.

I. Expression of Translationally altered RNA in a Monocotyledonous Plant to Confer Virus Resistance This aspect of the invention is directed to a general method for reducing the susceptibility of a monocotyledonous plant to infection by a virus by producing in the plant a transitionally altered RNA molecule corresponding to a messenger RNA sequence of the target virus.

The preferred approach for producing the translationally altered RNA molecule in a monocotyledonous plant is by introducing a chimeric gene designed to express this molecule into the genome of the plant. Such a chimeric gene will consist of at least two components, a promoter and a coding sequence which is operably linked to the promoter.

The promoter component may be any promoter which is capable of regulating or directing the expression of an operably linked gene in the targeted monocotyledonous plant. Such promoters are well known in the art. Preferably, a promoter which is capable of directing strong constitutive expression is used. Such promoters include, but are not limited to, the maize ubiquitin promoter described in Toki et al., *Plant Physiol.* 10:1503–1507 (1992), the maize phosphoenolpyruvate carboxylase (PEPC) promoter as described in Hudspeth, R. L. et al., *Plant Molec. Biol.* 12: 579–589 (1989), and the CaMV 35S promoter as described in Kay et al., *Science* 236: 1299–1302(1987).

The coding sequence component comprises a sequence which, when transcribed, produces a translationally altered RNA molecule corresponding to a target viral sequence. The target viral sequence is a messenger RNA (mRNA) molecule of the target virus, or a portion thereof. Since the target viral sequence is naturally translatable when a translation initiation codon is present, it is modified so as to render it translationally altered. For any given target viral sequence, the skilled artisan will be able to determine various modifications which could be made to render the resulting RNA molecule translationally altered.

Translation of an mRNA molecule in a plant cell generally requires the presence of an initiation AUG codon followed by an uninterrupted string of amino acid codons (known as the reading frame) ending with a translational stop codon, which may be either UAA, UAG or UGA. A DNA molecule encoding a translatable mRNA molecule may be modified to encode a translationally altered RNA, for instance, by either removing the initiation ATG codon, interrupting the reading frame, adding premature stop codons, or by a combination of these modifications.

Introduction of one or more premature stop codons (encoded by DNA codons TAA, TAG or TGA) in a target viral sequence may be accomplished by adding or deleting nucleotides or by modifying existing nucleotides using standard techniques such as site directed mutagenesis or mutagenesis by PCR. Adding or deleting nucleotides may have the additional benefit of interrupting the reading frame, which also has the effect of translationally altering the RNA molecule. While the addition of a premature stop codon anywhere along the length of the target viral sequence will render it translationally altered as that term is used herein to describe the invention, it is preferable to introduce such stop codons near the 5' end of the target viral mRNA so that any attenuated peptides which may be produced via partial translation are 20 amino acids or less in length.

The reading frame of a target viral sequence may be interrupted by the addition or deletion of nucleotides in the DNA coding sequence. As with the addition of premature stop codons, it is preferable to interrupt the reading frame near the 5' end of the target viral RNA so that any attenuated peptides corresponding to a portion of the peptide encoded by the target viral RNA which may be produced via partial translation are 20 amino acids or less in length.

Another way to translationally alter the target viral sequence is to remove the translation initiation codon, which will be an ATG. This may be accomplished simply by choosing a target viral sequence which does not include the translation initiation codon. Alternatively, this may be accomplished by disrupting the ATG codon either by adding, deleting or modifying nucleotides within this codon using standard techniques.

Any messenger RNA molecule produced by the target monocotyledonous virus, or any portion of such a molecule, may be used as the target viral sequence. The target viral sequence is preferably at least 120 nucleotides in length, more preferably at least 250 nucleotides in length, and most preferably at least 500 nucleotides in length.

A translationally altered viral RNA according to the invention includes any modified form of a naturally occurring viral messenger RNA sequence which cannot be completely translated as compared to the unmodified, naturally occurring form. Thus a translationally altered viral RNA may either be incapable of being translated at all, or it may be capable of translating an attenuated peptide corresponding to a portion of the peptide encoded by the target viral sequence used as a template.

The inhibitory effect of a translationally altered viral RNA is contemplated to be based, at least in part, upon its effect on host cell degradation mechanisms. Production of a translationally altered viral RNA in a plant cell is contemplated to trigger one or more cellular RNA degradation mechanisms which target the translationally altered viral RNA, as well as any corresponding homologous unaltered viral RNA molecules which may be present in the cell (see, e.g. page 550 of Dougherty, W. G. et al., *Mol. Plant-Microbe Int.* 7(5): 544–552 (1994); Chasan, R., *The Plant Cell* 6: 1329–1331 (1994)).

The ability to translate an attenuated peptide, particularly a short peptide less than 20 amino acids, is contemplated to enhance the triggering effect of the translationally altered viral RNA upon host cell RNA degradation pathways contemplated to play a role in inhibition of viral infection. Thus translationally altered RNAs which are capable of translating an attenuated peptide are preferred. More preferably, the translationally altered viral RNA is capable of translating an attenuated peptide less than 20 amino acids in length. For target viral RNAs which do not include a translation initiation codon, one may be added in conjunction with the addition of a premature stop codon or interruption of the reading frame to create a translationally altered RNA capable of translating an attenuated peptide (see, for example, the construct pCIB5018 described in Example 4).

The target viral sequence may correspond to the coding sequence for any viral protein, such as a viral coat protein, replicase, proteinase, inclusion body protein, helicase, 6K protein and VPg. Such sequences are well known for several monocotyledonous viruses including, but not limited to, MDMV (see SEQ ID NO. 1), Sugarcane mosaic virus (partial sequence; see Frenkel, M. J. et al. *J. Gen. Virol.* 72:237–242, (1991)), Johnsongrass mosaic virus (partial sequence) (see Gough, K. H. et al., *J. Gen. Virol.* 68:297–304, (1987), maize chlorotic mottle virus (see Nutter, R. C. et al. *Nucleic Acids Research* 17:3163–3177, (1989)), maize chlorotic dwarf virus (see international patent application no. PCT/US94/03028 published Sep. 29, 1994 as WO 94/21796), maize rough dwarf virus (partial sequence) (see Marzachi, C. et al. *Virology* 180:518–526, (1991)), maize stripe virus (partial sequence) (see Huiet, L. et al. *Virology* 182:47–53, (1991); Huiet, L. et al. *J. Gen. Virol.* 73:1603–1607, (1992); Huiet, L. et al. GenBank Accession Number L3446, (1993)), maize streak virus (see Mullineaux, P. M. et al *EMBO J.* 3:3063–3068, (1984)), barley yellow dwarf virus (see Larkins, B. A. et al. *J. Gen. Virol.* 72:2347–2355, (1991)), and wheat spindle streak virus (partial sequence) (see Sohn, A. et al. *Arch. Virol.* 135:279–292, (1994)).

Suitable host plants which may benefit from the production of translationally altered viral RNA include any monocotyledenous species which are susceptible to viral infection, particularly infection by a member of the potyvirus family. In particular, suitable host plants inlcude maize, wheat, sugarcane and sorghum.

In a preferred embodiment, the target viral sequence used is a coding sequence which is identical or highly homologous among two or more monocotyledonous viruses or virus strains. Expression of a translationally altered RNA in a monocotyledonous plant based on such a shared sequence is contemplated to inhibit infection by any of the viruses which produce a messenger RNA having homology with the target viral sequence.

II. The Genomic Structure and Organization of Make Dwar Mosaw Virus, Strain B

This aspect of the present invention is based upon the elucidation and characterization by the inventors of the genomic structure and organization of strain B of maize dwarf mosaic virus (MDMV-B). Previously, only the genomic sequence of the MDMV-B coat protein was known (see Frenkel, M. J. et al.,*J. Gen. Virol.* 72: 237–242 (1991)).

The MDMV-B positive strand RNA genome is believed to be approximately 10,000 bases in length based on the length of other potyviruses. The sequence of 8530 nucleotides beginning at the 3' end of the MDMV-B genome is set forth in SEQ ID NO: 1. A single long open reading frame was identified within this sequence of the viral genome and the polyprotein amino acid sequence encoded by this open reading frame is provided in SEQ ID NO: 2. With the sequence information provided, this viral genome can be isolated and cloned using a variety of standard genetic engineering techniques well known to those of skill in the art Three DNA fragments covering 85% of the MDMV-B genome have been cloned into a Bluescript II SK plasmid backbone (Stratagene), transformed and propagated in the *E. coli* cell line HB101, and deposited on Jun. 29, 1995 with the Midwest Area National Center for Agricultural Utilization Research (formerly known as the National Regional Research Lab and still referred to by the corresponding acronym "NRRL"). One of the plasmids designated "1-47" contains nucleotides 3252–8530 of the MDMV-B genome (NRRL No. B-21479). Another plasmid designated "2-24" contains nucleotides 1866–3317 of the MDMV-B genome (NRRL No. B-21480). Yet another plasmid designated "9-1-5" contains nucleotides 1–2122 of the MDMV-B genome (NRRL No. B-21481).

The polyprotein encoded by the MDMV-B genome includes a single coat protein designated CP whose coding sequence extends from nucleotide 7308 to 8291 of SEQ ID No. 1 and whose amino acid sequence extends from amino acid 2436 to 2763 of SEQ ID No. 2. The MDMV-B polyprotein is also contemplated to include a replicase protein, three proteinases, a 6K protein, a helper component, proteins involved in viral movement in the host plant (both cell to cell and long distance transport), a helicase protein and a VPg protein.

MDMV-B is contemplated to contain a serine-like proteinase analogous to serine-like proteinases that have been identified in related potyviruses. These serine-like proteinases have a characteristic catalytic domain of three amino acids consisting of a histidine at position 1 of the domain, an aspartic acid at the second position, and a cysteine at the third (see Bazan, J. F. and Fletterick, R. J., *Proc. Natl. Acad. Sci. USA* 85: 7872–7876 (1988)). These amino acids are separated in the primary amino acid sequence by a region spanning approximately 140 amino acids. The intervening sequences between each of the catalytic domain sequences exhibits additional limited homology among the known proteinases (see Bazan, J. F. and Fletterick, R. J., *Proc. Natl. Acad. Sci. USA* 85: 7872–7876 (1988)). Based upon comparison with the known proteinase sequences, the MDMV-B proteinase catalytic domain is contemplated to span a 105 amino acid sequence from position 1718 to 1823 of SEQ ID No: 2 with the three catalytic residues occurring at amino acids 1718, 1753, and 1823 of SEQ ID No. 2.

MDMV-B is also contemplated to contain a second proteinase analogous to the cysteine proteinases that have been identified in related potyviruses. The active-site residues form a catalytic diad made up of a conserved cysteine and histidine which are separated by 72 amino acids (see Oh, C. and Carrington, J. C., *Virology* 173:692–699, (1989)). This proteinase is located within the carboxy-terminus of the HC-Pro region of the potyvirus polyprotein. Based upon comparison with the known proteinase sequences of tobacco etch virus, the MDMV-B HC-Pro proteinase domain is contemplated to span a 74 amino acid region from position 263 to 336 of SEQ ID No: 2 with the two catalytic residues occurring at amino acids 263 and 336.

The location of the MDMV-B putative helicase domain can be identified based on the homology with other known viral helicase domains (see Gorbalenya, A. E. et al., *Nucleic Acids Research* 17 (12):4713–4730, (1989)). The helicase domain consists of seven distinct highly conserved segments which correspond to the NTP-binding motif. The primary consensus site consists of a glycine at position 1 of the motif, glycine at position 3, lysine at position 4, and either a serine or threonine at position 5 (see Gorbalenya, A. E. et al. supra). The conserved helicase domain is located in the MDMV-B genome within a region encoding the cylindrical inclusion protein (CIP) and is found from amino acids 880 to 1010 of SEQ ID No: 2. The conserved domain (GxGDS) is located at amino acids 883, 885, 886, and 887 of SEQ ID No: 2.

The coding sequence for the replicase gene of MDMV-B may also be determined by the location of conserved motifs common to viral replicase genes and by identification of putative viral proteinase cleavage sites bordering the replicase coding sequence. Conserved motifs have been found in other viral replicases. In particular, the conserved amino acid motif GDD (known as domain C) is the hallmark consensus sequence for all RNA-dependent replicases loch et al. *EMBO* 8: 3867–3874 (1989)). This conserved motif is found at amino acids 2266–2268 in the MDMV-B open reading frame (SEQ ID No: 2). Two additional conserved motifs characteristic of a plant viral replicase have been identified and designated as domain A and B (Poch et al., supra). Domain A is a 17 amino acid sequence with two centrally conserved amino acids which are present in the MDMV-B genome at amino acids 2163 and 2168 of SEQ ID No: 2. Domain B is a 10 amino acid sequence consisting of 5 conserved amino acids which are present in the MDMV-B genome at amino acids 2222, 2223, 2224, 2225 and 2226 of SEQ ID No: 2.

A. Virus Resistance Approaches utilizing Structural Information Provided for MDMV-B The isolated MDMV-B genomic sequences taught by the present invention are particularly useful for the development of viral resistance in susceptible host plants. With the information provided by the present invention, several approaches for inhibiting plant virus infection in susceptible plant hosts which involve expressing in such hosts various inhibitory transcripts or proteins derived from the target virus genome may now be applied to MDMV.

Use of translationally altered RNA to confer monocotyledonous virus resistance as described herein above may now be applied to MDMV-B, as demonstrated by Example 4.

Another approach which may be used to confer plant virus resistance is to express the replicase gene of the target virus in the host plant (e.g. international patent application pub. nos. WO94/18336 pub. Aug. 18, 1994 to Tumer et al. for potato leaf roll virus and WO 91/13542 pub. Sep. 19, 1991 to Zaitlin et al. for tobacco mosaic virus; herein incorporated by reference in their entirety). This approach may also be applied to MDMV-B using the information provided by the present invention.

For resistance strategies which depend upon expression of a viral replicase coding sequence in a transgenic plant, a cDNA clone encompassing nucleotides 5745 to 7307 of SEQ ID No: 1, contemplated to include the active domains of the MDMV-B replicase can be used for plant transformation. More preferably, such strategies may be employed by transforming a plant with larger expressible fragments of the MDMV-B genome contemplated to encompass the entire replicase protein. In this case, the MDMV-B replicase would be cleaved from the encoded polypeptide when exposed to MDMV-B viral proteinase in the plant cell.

The MDMV-B replicase coding sequence may be engineered for recombinant expression in a monocotyledonous host plant which is normally susceptible to infection by MDMV-B. Expression of MDMV-B replicase in such a monocotyledonous host plant is contemplated to confer resistance to (i.e. inhibit) MDMV-B infection.

Suitable host plants which may benefit from application of any of the resistance approaches described above include any monocotyledonous species which are susceptible to infection by MDMV-B. In particular, suitable host plants are contemplated to include maize, sorghum and sugarcane.

To express inhibitory transcripts or proteins derived from the MDMV-B genome in a host plant cell, the corresponding coding sequence is operably linked to regulatory sequences which cause its expression in the chosen host plant cell. Examples of promoters capable of functioning in plants or plant cells, i.e., those capable of driving expression of the associated coding sequences such as MDMV-B CP in plant cells, include the cauliflower mosaic virus (CaMV) 19S or 35S promoters and CaMV double promoters; nopaline synthase promoters; pathogenesis-related (PR) protein promoters; small subunit of ribulose bisphosphate carboxylase (ssuRUBISCO) promoters, and the like. Preferred are the rice actin promoter (McElroy et al, *Mol. Gen. Genet.* 231:

150 (1991)), maize ubiquitin promoter (EP 0 342 926; Taylor et al., *Plant Cell Rep.* 12: 491 (1993); Toki et al., *Plant Phys.* 100:1503–1507 (1992)), a maize pith-preferred promoter (international patent application no. PCT/US92/08476 published Apr. 15, 1993 as WO 93/07278, incorporated by reference herein in its entirety; in particular see FIG. 24 and pages 27–28), and the Pr-1 promoter from tobacco, Arabidopsis, or maize (see European Patent Application publication No. 332,104 published Sep. 13, 1989). Also preferred are the 35S promoter and an enhanced or double 35S promoter such as that described in Kay et al., *Science* 236: 1299–1302 (1987) and the double 35S promoter cloned into pCGN2113, deposited as ATCC 40587. The promoters themselves may be modified to manipulate promoter strength to increase expression of MDMV-B coding sequences in accordance with art-recognized procedures.

The chimeric DNA construct(s) of the invention may contain multiple copies of a promoter or multiple copies of a particular coding sequence. In addition, the construct(s) may include coding sequences for markers and coding sequences for other peptides such as signal or transit peptides, each in proper reading frame with the other functional elements in the DNA molecule. The preparation of such constructs are within the ordinary level of skill in the art.

Since the MDMV-B proteins are naturally expressed as part of a polyprotein, each protein does not include its own translation initiation and translation stop codon. To express such proteins individually in the context of a chimeric gene, a translation initiation codon will need to be added immediately adjacent to the first codon if one does not occur as part of the coding sequence. The skilled artisan will recognize that addition of such a translation initiation codon will add a methionine amino acid to the end of the encoded protein. Such an addition is not contemplated to have any significant effect upon the properties of the protein. Also, a translation stop codon will need to be added to the chimeric gene immediately after the last codon of the protein if one does not naturally occur at this location.

Useful markers include peptides providing herbicide, antibiotic or drug resistance, such as, for example, resistance to hygromycin, kanamycin, G418, gentamycin, lincomycin, methotrexate, glyphosate, phosphinothricin, or the like. These markers can be used to select cells transformed with the chimeric DNA constructs of the invention from untransformed cells. Other useful markers are peptidic enzymes which can be easily detected by a visible reaction, for example a color reaction, for example luciferase, β-glucuronidase, or β-galactosidase.

EXAMPLES

Standard recombinant DNA and molecular cloning techniques used here are well known in the art and are described by J. Sambrook, E. F. Fritsch and T. Maniatis, *Molecular Cloning: A Laboratory manual*, Cold Spring Harbor laboratory, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984).

Example 1

Construction of Plant Transformation Vectors

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene which confers resistance to kanamycin and related antibiotics (Messing & Vierra, *Gene* 19: 259–268 (1982); Bevan et al., *Nature* 304:184–187 (1983)), the bar gene which confers resistance to the herbicide phosphinothricin (White et al., *Nucl. Acids Res.* 18: 1062 (1990), Spencer et al., *Theor. Appl. Genet.* 79: 625–631(1990)), the hph gene which confers resistance to the antibiotic hygromycin (Blochinger & Diggelmann, *Mol Cell Biol* 4: 2929–2931), and the dhfr gene, which confers resistance to methotrexate (Bourouis et al., *EMBO J.* 2(7): 1099–1104 (1983)).

(1) Construction of Vectors Suitable for Agrobacterium Transformation

Many vectors are available for transformation using *Agrobacterium tumefaciens*. These typically carry at least one T-DNA border sequence and include vectors such as pBIN19 (Bevan, *Nucl. Acids Res.* (1984)) and pXYZ. Below the construction of two typical vectors is described.

Construction of pCIB200 and pCIB2001

The binary vectors pCIB200 and pCIB2001 are used for the construction of recombinant vectors for use with Agrobacterium and was constructed in the following manner. pTJS75kan was created by NarI digestion of pTJS75 (Schmidhauser & Helinski, *J Bacteriol.* 164: 446–455 (1985)) allowing excision of the tetracycline-resistance gene, followed by insertion of an AccI fragment from pUC4K carrying an NPTII gene (Messing & Vierra, *Gene* 19: 259–268 (1982); Bevan et al., *Nature* 304: 184–187 (1983); McBride et al., *Plant Molecular Biology* 14: 266–276 (1990)). XhoI linkers were ligated to the EcoRV fragment of pCIB7 which contains the left and right T-DNA borders, a plant selectable nos/nptII chimeric gene and the pUC polylinker (Rothstein et al., *Gene* 53: 153–161 (1987)), and the XhoI-digested fragment was cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 which was created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives thereof

The binary vector pCIB10 contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al., *Gene* 53: 153–161 (1987). Various derivatives of pCIB10 have been constructed which incorporate the gene for hygromycin B phosphotransferase described by Gritz et al., *Gene* 25: 179–188 (1983)). These derivatives enable selection of transgenic plant cells on hygromycin only (pCIB743), or hygromycin and kanamycin (pCIB715, pCIB717).

(2) Construction of Vectors Suitable for non-Agrobacterium Transformation.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on Agrobacterium include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites were mutated using standard PCR techniques in such a way as to remove the ATGs and generate the restriction sites SspI and PvuII. The new restriction sites were 96 and 37 bp away from the unique SalI site and 101 and 42 bp away from the actual start site. The resultant derivative of pCIB246 was designated pCIB3025. The GUS gene was then excised from pCIB3025 by digestion with SalI and SacI, the termini rendered blunt and re-ligated to generate plasmid pCIB3060. The plasmid pJIT82 was obtained from the John Innes Centre, Norwich and a 400 bp SmaI fragment containing the bar gene from *Streptomyces viridochroinogenes* was excised and inserted into the HpaI site of pCIB3060 (Thompson et al. *EMBO J* 6: 2519–2523 (1987)). This generated pCIB3064 which comprises the bar gene under the control of the CaMV 35S promoter and terminator for herbicide selection, a gene fro ampicillin resistance (for selection in *E. coli*) and a polylinker with the unique sites SphI, PstI, HindIII, and BamHI. This vector is suitable for the cloning of plant expression cassettes containing their own regulatory signals.

Construction of pSOG19 and pSOG35 pSOG35 is a transformation vector which utilizes the *E. coli* gene dihydrofolate reductase (DHR) as a selectable marker conferring resistance to methotrexate. PCR was used to amplify the 35S promoter (~800 bp), intron 6 from the maize Adh1 gene (~550 bp) and 18 bp of the GUS untranslated leader sequence from pSOG10. A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences.

Example 2

Construction of Plant Expression Cassettes

Gene sequences intended for expression in transgenic plants are firstly assembled in expression cassettes behind a suitable promoter and upstream of a suitable transcription terminator to create a chimeric gene. These expression cassettes can then be easily transferred to the plant transformation vectors described above in Example 1.

Promoter Selection

The selection of a promoter used in expression cassettes or chimeric genes will determine the spatial and temporal expression pattern of the transgene in the transgenic plant Selected promoters will express transgenes in specific cell types (such as leaf epidermal cells, mesophyll cells, root cortex cells) or in specific tissues or organs (roots, leaves or flowers, for example) and this selection will reflect the desired location of expression of the transgene. Alternatively, the selected promoter may drive expression of the gene under a light-induced or other temporally regulated promoter. A further alternative is that the selected promoter be chemically regulated This would provide the possibility of inducing expression of the transgene only when desired and caused by treatment with a chemical inducer.

Transcriptional Terminators

A variety of transcriptional terminators are available for use in expression cassettes. These are responsible for the termination of transcription beyond the transgene and its correct polyadenylation. Appropriate transcriptional terminators and those which are known to function in plants and include the CaMV 355 terminator, the tml terminator, the nopaline synthase terminator, the pea rbcS E9 terminator. These can be used in both monocotyledons and dicotyledons.

Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1: 1183–1200 (1987)). In the same experimental system, the intron from the maize bronzel gene had a similar effect in enhancing expression (Callis et al., supra). Intron sequences have been routinely incorporated into plant transformation vectors, typically within the non-translated leader.

A number of non-translated leader sequences derived from viruses are also known to enhance expression. Specifically, leader sequences from Tobacco Mosaic Virus FMV, the "W-sequence"), Maize Chlorotic Mottle Virus (MCMV), and Alfalfa Mosaic Virus (AlMV) have been shown to be effective in enhancing expression (e.g. Gallie et al. *Nucl. Acids Res.* 15: 8693–8711 (1987); Skuzeski et al. *Plant Molec. Biol.* 15: 65–79 (1990))

Example 3

Transformation of Monocotyledons

Transformation of monocotyledon species such as wheat or maize has become routine. Preferred techniques include direct gene transfer into protoplasts using PEG or electroporation techniques, and particle bombardment into callus tissue. Transformations can be undertaken with a single DNA species or multiple DNA species (ie. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4: 1093–1096 (1986)).

Patent Applications EP 0 292 435 (to Ciba-Geigy), EP 0 392 225 (to Ciba-Geigy) and WO 93/07278 (to Ciba-Geigy) describe techniques for the preparation of callus and protoplasts from an élite inbred line of maize, transformation of protoplasts using PEG or electroporation, and the regeneration of maize plants from transformed protoplasts. Gordon-Kamm et al., *Plant Cell* 2: 603–618 (1990)) and Fromm et al., *Biotechnology* 8: 833–839 (1990)) have published techniques for transformation of A188-derived maize line using particle bombardment Furthermore, WO 93/07278 (to Ciba-Geigy) and Koziel et al., *Biotechnology* 11: 194–200 (1993)) describe techniques for the transformation of élite inbred lines of maize by particle bombardment. This technique utilizes immature maize embryos of 1.5–2.5 mm length excised from a maize ear 1415 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., *Plant Cell Rep* 7: 379–384 (1988); Shimamoto et al. *Nature* 338: 274–277 (1989); Datta et al. *Biotechnology* 8: 736–740 (1990)). Both types are also routinely transformable using particle bombardment (Christou et al. *Biotechnology* 9: 957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation has been described by Vasil et al., *Biotechnology* 10: 667–674 (1992)) using particle bombardment into cells of type C long-term regenerable callus, and also by Vasil et al., *Biotechnology* 11: 1553–1558 (1993)) and Weeks et al., *Plant Physiol.* 102: 1077–1084 (1993) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (see Murashige & Skoog, *Physiologia Plantarum* 15: 473–497 (1962)) and 3 mg/l 2,4-D for induction of somatic embryos which is allowed to proceed in the dark. On the chosen day of bombardment, embryos are removed from the induction medium and placed onto the osmoticum (ie. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics helium device using a burst pressure of ~1000 psi using a standard 80 mesh screen. After bombardment, the embryos are placed back into the dark to recover for about 24 h (still on osmoticum). After 24 hours, the embryos are removed from the osmoticum and placed back onto induction medium where they stay for about a month before regeneration. Approximately one month later the embryo explants with developing embryonic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent Example 4

MDMV-B Resistance Conferred by Expression of Translationally Altered Viral Transcripts The most prevalent virus infecting maize in the United States and Europe is maize dwarf mosaic virus (MDMV). Viral diseases of maize result in an estimated 5% annual yield reduction as well as reduce overall plant health which results in increased susceptibility to other pathogens. Experimental trials using common maize inbreds and hybrids have shown yield reductions from MDMV as great as 35% in inoculated plots. MDMV is a member of the potyvirus plant virus family and is composed of many taxonomic strains, with the two most common being strains A and B. These strains are differentiated by the ability of MDMV-A to infect johnsongrass which is the overwintering host. MDMV-A is primarily localized to the southeastern United States due to the occurrence of johnsongrass in this area. MDMV-B is more widespread and can be found in the U.S. corn belt and throughout Europe (i.e. Spain, France, and Italy). MDMV-B is the most economically important maize virus due to its widespread occurrence. Both strains of MDMV are transmitted in nature by aphids in a non-persistent manner, thus insect control is not a practical control method. The most effective method of control of these diseases is the use of resistant germplasm. In maize, sources of resistant germplasm exist to both strains of the MDMV, but the efficacy of the resistance is somewhat variable and identification of this material can be difficult. Studies have shown that resistance to MDMV is not the result of a single, dominant gene, rather being multigenic (2–5 genes). There has been an abundance of research on the development of alternative strategies for conferring resistance in transgenic plants. Most of these strategies have focused on the expression of viral genes (i.e. the viral coat protein) in plants as a means of conferring resistance. The benefits of these strategies are that the resistance can be developed to viruses in which effective natural resistance can not be identified and the resistance is more easily transferred to agronomically desirable plant lines. The majority of this work has focused on coat protein mediated resistance which is based on the expression of the viral coat protein in the plant. Coat protein mediated resistance has been particularly effective for some viruses (e.g. tobacco mosaic virus) but inconsistent for other viruses (e.g. potyviruses) when tested in model systems such as tobacco and in economically important grain crops such as maize, wheat, and rice. More recently, another virus resistance strategy has been developed which conferred an immune phenotype in plants transformed with segments of virus sequence. The phenomenon has been termed RNA-mediated resistance and is thought to be similar to sense suppression or co-suppression described in other plant systems. Specifically, plants were transformed with a sequence encoding the virus coat protein which had been modified to cause premature termination during translation. The expression of this untranslatable viral coat protein sequence at high levels was hypothesized to activate a RNA degradation cycle which eliminated the transgene mRNA in a sequence specific manner. The pathway was then believed to be capable of also eliminating an infecting virus which contains sequence highly homologous (>90%) to the transgene sequence. Since the original description of RNA-mediated resistance (see Lindbo, J. A. et al., *Mol. Plant-Microbe Int.* 5(2): 144–153 (1992) and DeHaan et al., *Bio/Technology* 10: 1133–1137 (1992)), there have been additional descriptions of this form of resistance. Furthermore, it has been shown that prior work thought to be resistance due to expression of a viral protein is more likely to be RNA-mediated resistance. However, this strategy has not been effective for all viruses (see Powell, P. A. et al., *Virology* 175: 124–130 (1990) and Fang, G. et al., *Mol. Plant-Microbe Int.* 6(3): 358–367 (1993)). The examples of RNA-mediated resistance have been limited to model dicot hosts such as tobacco and potato. It is not known if this resistance will be effective in monocots nor what factors will be necessary for induction of this resistance.

Our research has focused on cloning and sequencing the remainder of the MDMV-B genome. We have disclosed the majority of the MDMV-B sequence in this application. We have identified coding regions within the MDMV-B coding region based on conserved motifs previously identified in other potyviruses. The regions of the virus selected for use as transgenes have been the MDMV-B non-structural proteins (i.e. Replicase, Proteinase, and Helicase). These regions were targeted based on the expected higher degree of sequence conservation within these genes among strains of MDMV. We predict that the use of these regions will give the highest probability of obtaining resistance to multiple strains of MDMV when transformed into elite maize inbreds. The sequences have been used to transform maize plants for the purpose of conferring virus resistance.

MATERIALS AND METHODS

Maize dwarf mosaic virus strain B (MDMV-B) was obtained from Dr. S. Jensen (University of Nebraska-Lincoln) and maintained in a susceptible maize inbred by serial inoculation. Virus was prepared for inoculation as previously described (see Law, M. D. et al. *Phytopathology* 79:757–761, (1988)).

The virus was purified from two week old infected maize tissue by the following protocol. The harvested tissue was homogenized with 0.2 sodium acetate, pH 5.0 containing 0.1% β-mercaptoethanol (1:6 ratio W:V) in a blender. The homogenate was filtered through cheesecloth and then centrifuged for 15 minutes at 6000 RPM (Sorvall GSA rotor). The recovered supernatent was then filtered through glass wool and adjusted to a concentration of 0.5% Triton X-100 and 0.2M NaCl. The virus was precipitated from the solution by adding PEG 8000 (8% final concentration) and then sing for 2 hours at 4° C. The virus was recovered by centrifugation for 15 minutes at 8,000 RPM (Sorvall GSA rotor).

The resulting pellet containing the virus was resuspended by stirring in 0.1M Tris pH 6.5 containing 0.032 M sodium citrate. The virus solution was clarified by centrifugation through a 20% sucrose pad for 2 hours at 28,000 RPM (SW28 rotor). The recovered pellet was resuspended in 10 ml of 0.1M Tris pH 6.5 containing 0.032 M sodium citrate. The supernatent was adjusted to a concentration of 34% cesium sulfate and centrifuged for 14 hours at 48,000 RPM (Ti 70.1 rotor). The opalescent band containing the virus was removed and dialyzed against 0.1M Tris pH 6.5 containing 0.032 M sodium citrate. Viral RNA was isolated from the purified virions by phenol extraction and ethanol precipitation.

The isolated RNA was then used as template for cDNA preparation using oligo dT primers. The preparation of cDNA clones were performed by standard procedures as described (see Sambrook, J. et al., iMolecular Cloning: A Laboratory Manual", Cold Spring Harbor Laboratory Press, (1989)).

Constructs were prepared to specific regions of the MDMV-B genome by PCR amplification from cDNA clones. The region amplified by PCR was typically 1200 to 1400 nucleotides in length and was confirmed by sequencing. Constructs were prepared to the regions of the MDMV-B genome which encode the viral replicase (NIb), proteinase (NIa), and cylindrical inclusion protein (CIP). These regions were selected based on the higher sequence conservation within these regions between members of the potyvirus family. The constructs corresponding to a specific viral coding region were altered during PCR amplification by nucleotide substitutions within the primers. A methionine translation initiation codon was generated at the first codon preceding the first native codon and a termination codon was created at the seventh codon in all constructs tested. This would create a mRNA only capable of translating small peptides. The constructs were then ligated into either the pUBA plasmid (see Toki et al. *Plant Physiol* 100:1503–1507, (1992)) or the pCIB4421 plasmid. The pUBA plasmid contained the Ubiquitin promoter and the NOS terminator while pCIB4421 contained the maize phosphoenolpyruvate carboxylase (PEPC) promoter and the 35S terminator. The plasmid constructs were then verified by DNA sequencing.

The constructs used in this example to transform maize plants have been designated pCIB5018 and pCIB 5019. pCIB5018 was constructed by ligating the PCR amplified NIa fragment (nucleotides 4452–5744 of SEQ ID No. 1) into pCIB442 1. The NIa fragment used for ligation had previously been altered by insertion of an ATG immediately before the first nucleotide of the first codon (i.e. the G at position 4452 of SEQ ID No. 1) and substitution of a thymidine (T) for the adenine (A) at nucleotide 4470 of SEQ ID No. 1 to create a premature stop codon. pCIB5019 was constructed by ligating the altered NIa fragment described above into the pUBA plasmid.

Microprojectile Bombardment Protocols

Plasmid DNA was precipitated onto 1 μm gold microcarrier particles as described in the DuPont Biolistic manual. 5 μg of plasmid DNA containing a synthetic phosphinothrycin acetyltransferase selectable marker gene and 5 μg of either pCIB5018 or pCIB5019 were added per 50 μl of prepared microcarrier. The synthetic phosphinothrycin acetyltransferase selectable marker gene provides resistance to the same selection agents as the BAR gene (see Kramer, C. et al. *Planta* 190: 454–458 (1993)). Bombardment of tissue was carried out with the DuPont PDS-1000He Biolistic® device. An additional 150×150 mesh/linear inch screen was inserted 2 cm below the stopping screen. Immature embryos were bombarded with 1550 psi rupture discs on a plate angled 6–8 cm below the stopping screen to maximize scutellum exposure to particles. Type I callus was placed 4 cm below the stopping screen and 900 psi rupture discs were used in bombardment. All plates for both explant types were bombarded twice.

Immature Embryo Explant Source Initiation and Selection

Immature embryos of a proprietary Ciba elite line (CG00526) were used as the initial explant source in microprojectile-mediated transformation. Embryos were excised from the ears 10–14 days post-pollination, when 1–2 mm in length. After surface sterilization in a 10% Clorox solution, embryos were plated embryonic axis down on the surface of the agar-solidified medium Embryos were plated onto Duncan's "D" callus induction medium plus 5 mg/l chloramben, 2% sucrose, 12 mM proline and either the organic amendments specified in Duncan's (2DG4) or a modified version (2DA1) which omits the casein hydrolysate and adds the amino acids minus glutamine and asparagine from Kao and Michayluk's "KM" medium (see Kao and Michayluk, *Planta* 126:105–110, (1975)). The plated embryos were kept in a 25° C. dark culture room continuously until the regeneration phase was initiated. The day after plating the embryos were transferred to the appropriate G4 or A1 media containing 12% sucrose at least four hours prior to microprojectile bombardment. Thirty-six embryos were arranged in a 2–3 cm circle in the center of the plate. The embryos remain on the 12% sucrose plate overnight after bombardment. The following day, embryos were transferred either to 2DG4+5 chloramben+the equivalent of a 10 mg/l concentration of Basta®herbicide (glufosinate ammonium) or 2DA1+5 chloramben+5 mg/l Basta.

Fourteen days from the initial excision and plating, developing compact, organized type I callus was excised from the original explant and subcultured to either 2DG4+0.5 mg/l 2,4D+10 mg/l Basta or 2DA1+0.5 mg 2,4-D+5 mg/l Basta. Viable, healthy callus was serially subcultured every fourteen days during the selection phase. All tissue was then transferred to Duncan's medium, modified by omitting all amino acids, plus 2% sucrose, 0.5 mg/l 2,4D and 10 mg/l Basta (2DG8) at the end of eight weeks. After a two week passage on the G8 medium, all living tissue was transferred to regeneration medium.

Type I Explant Source Initiation and Selection

Immature embryos of the Ciba elite line (CG00526) were plated embryonic axis down onto 2DG4+5 chloramben at the 1–2 mm length size. The developing compact, highly organogenic (type I) callus was excised from the original embryo explant after fourteen days and maintained serially on 2DG4+0.5 mg/l 2,4D by subculturing to fresh medium every ten-fourteen days. When the callus lines obtained were two to three months old, they were prepared for microprojectile bombardment. The tissue was subcultured to fresh medium in small pieces approximately 1–3 mm in size one to two days prior to bombardment. On the day of bombardment, the tissue was arranged in a 2–3 cm circle in the center of a DA1 plate containing 12% sucrose and 0.5 mg/l 2,4D at least four hours prior to bombardment. The callus was kept on the plate after bombardment overnight, and transferred the next day to 2DA1+0.5 mg/l 2,4D+10 mg/lBasta. Viable, healthy callus was serially subcultured on the same medium every fourteen days during the selection phase. All tissue was transferred to Duncan's medium, modified by omitting all amino acids, plus 2% sucrose, 0.5 mg/l 2,4-D and 10 mg/l Basta (2DG8) at the end of eight weeks. After a two week passage on the G8 medium, all living tissue was transferred to regeneration medium.

Regeneration and Plantlet Establishment of Immature Embryo and Type I Explant Source Experiments Tissue for regeneration was moved to a 25° C. light culture room under a 16 hour photoperiod. Regeneration medium consisted of Murashige and Skoog's (MS) salts and vitamins, 3% sucrose+0.25 mg/l ancymidol, 1.0 mg/l NAA, 0.5 mg/l kinetin and 5 mg/l Basta. After a two week passage on the regeneration medium with growth regulators, the tissue was transferred to MS medium+3 mg/lBasta and no additional growth regulators. Plantlets reaching 1–3 cm length were transferred from plates to Magenta®GA-7 boxes containing MS medium (0.75×concentration+1% sucrose) and no Basta for root development. Plantlets with sufficient root development were transplanted to soil and moved to the greenhouse. Plantlets were hardened off in a 70% humidity phytotron for one to two weeks before moving the plants to the greenhouse range. The greenhouse conditions were as follows: 55% humidity, 400 Einsteins light intensity, 16 hour photoperiod, 80–84° F. Day temperature, 64–68° F. Night temperature. Plants were allowed to grow to maturity in the greenhouse and were either selfed or backcrossed to the parental line in the $T_1$ generation.

Analysis of $T_1$ Plants $T_0$ plantlets were first assayed by polymerase chain reaction (PCR) to detect the selectable marker, the gene of interest and an alcohol dehydrogenase (Adh) gene sequence as an internal assay control. Plantlets were assayed at approximately eight to fourteen cm height, when the plantlets were still in the GA-7 boxes. Standard PCR conditions were used (see Kramer, C. et al. *Planta* 190: 454–458 (1993)). The Adh internal control primer pair sequence was TGCATGTCGGTTGTGTTGCA (SEQ ID NO. 3) and CTCAGCAAGTACCTAGACCA (SEQ ID No. 4). The primer pair sequence for the synthetic PAT gene was TGTCTCCGGAGAGGAGACC (SEQ ID No. 5) and CCAACATCATGCCATCCACC (SEQ ID No. 6). The primer pair sequence for the NIa proteinase gene is GCGGGATCCATGGGGAAGAACAAACGCAGTrGA (5') (SEQ ID No. 7) and GCGGAGCTCTTACTCTTCAACGCTCGCGTC (3') (SEQ ID No. 8). The parameters for PCR amplification for all primer pairs were 45 sec at 94° C., 30 sec at 62° C., 30 sec at 72° C. plus a 3 sec/cycle extension elongation for 40 cycles.

Plantlets identified by PCR to be transformed were analyzed by Northern blot assay for mRNA transcript of the gene of interest (NIa proteinase). Plants were assayed for mRNA expression either while in the GA-7 containers or when the plants had been acclimated in the greenhouse. The probe was a 1303 bp fragment of the NIa gene excised by a BamH1/Sac restriction digest of the pCIB5019 plasmid. Labeling was carried out with the Gibco/BRL RadPrime DNA Labeling kit as described by the manufacturer. Northern blot protocols were performed as described (see Sambrook, J. et al., "Molecular Cloning: A Laboratory Manual", Cold Spring Harbor Laboratory Press, (1989)).

Analysis of $T_1$ Plants $T_1$ seed harvested from the $T_0$ plants was first dried down in the drying room for one to two weeks before planting. Seed were planted directly in flats and watered in. The flats were bottom watered with either a 0.15% volume/volume Basta solution or with water two days after planting. Four different transformation events were tested for herbicide and disease resistance in this example, as well as the wild-type elite control. Forty seeds from each individual transformed plant were tested initially, 20 in Basta and 20 in the water control. Seven days after the first Basta drench, a second drench was carried out in the same manner.

All plants were inoculated with MDMV-B following the second Basta soil drench when the plants were 4–5 inches in height (3–5 Leaf Stage). A second virus inoculation was performed on all plantlets 4–6 days after the first inoculation to insure infection. Plants were scored for viability in the plus and minus Basta drench and for the presence or absence of viral symptoms at the end of two and a half weeks.

Plants which showed resistance to the virus, as measured by the absence of viral symptoms, and a susceptible sibling were assayed by Northern blot analysis using the NIa fragment as described above. The resistant plants were also assayed by ELISA and Western blot analysis for the presence of MDMV-B coat protein in the plants.

ELISA and Western Blot analysis of the transgenic plants.

The primary antibody used for both assays was a polyclonal antibody specific for the MDMV-B coat protein which was obtained from Dr. S. Jensen (University of Nebraska-Lincoln). The second antibody was an affinity purified polyclonal IgG alkaline phosphatase labeled goat anti-rabbit antibody (Kirkegard and Perry Laboratories, Gaithersburg, Md.).

ELISA Analysis

Tissue samples were taken from all plants not exhibiting characteristic MDMV-B symptoms and from one infected plant. Samples were also taken from healthy and infected CG00526 plants as controls. The samples (two leaf punches—1 cm in diameter) were taken from both the inoculated leaf and the youngest available leaf. The tissue samples were homogenized in 0.400 ml of borate buffered saline (100 mM boric acid, 25 mM sodium borate, 75 mM sodium chloride). Aliquots (50 μl) of each sample were applied to a ethanol washed ELISA plate and incubated overnight at 4° C. The plates were then washed once with ELISA wash buffer (10 mM Tris-HCl, 0.05% Tween-20, 0.02% sodium azide), and blocked with ELISA block/diluent (10 mM sodium phosphate, 140 mM sodium chloride, 0.05% Tween-20, 1% BSA, 0.02% sodium azide) for one hour at room temperature. The plates were washed three times with ELISA wash buffer. The primary antibody was applied at a 1:5000 dilution in 50 μl of ELISA block/diluent and incubated for 2 hours at 37° C. and then washed three times with ELISA wash buffer. The second antibody was applied at a concentration of 1.5 μg/ml in ELISA block/diluent and incubated for 2 hours at 37° C. The plates were washed three times with ELISA wash buffer and were developed by incubation in ELISA substrate (Kirkegard and Perry) for 30 minutes at room temperature. The reaction was stopped by the addition of 50 μl of 3M sodium hydroxide. The plates were read with a SLT 340 ATTC ELISA plate reader (SLT Labinstruments) at 405 nm.

Western Blot Analysis

Western blot analysis was performed on samples used for ELISA analysis. A 2 μl aliquot of the samples was diluted into 10 μl of 1× loading dye (Novex Inc). The samples were electrophoresed on an 8%–16% Tris-glycine polyacrylamide gel (Novex) in Tris running buffer (25 mM Tris-Base, 192 mM glycine, 0.1% SDS) at 120 volts for approximately 2.5 hours. The gel was blotted onto nitrocellulose using a Biorad blotting apparatus in transfer buffer (25 mM Tris-Base, 192 mM glycine, and 10% methanol) at 120 volts for 45 minutes. The filter was blocked with blocking/diluent (1× TBS, (20 mM Tris-Base, 500 mM NaCl, pH 7.5), 0.05% Tween-20, 1% BSA, 5% lamb serum) at room temperature for 45 minutes. The filter was incubated with the primary antibody, described above, at a dilution of 1:1000 in blocking/diluent at room temperature for 1.25 hours. The filter was washed for five minutes in 1× TTBS, (1× TBS, 0.05% Tween-20). The second antibody, described above, was incubated with the filter in blocking/diluent at a dilution of 1:1000, for 1.25 hours at room temperature. The filters were washed twice for 5 minutes in 1× TTMS followed by a single wash in 1× TBS for 5 minutes. The filter was developed with Nitro Blue Tetrazolium (NBT) and 5-bromo4-chloro-3-indolyl phosphatase (BCIP) in 0.1M Tris-HCl pH 9.5 as described by the manufacturer. The filter was developed for approximately 20 minutes and then stopped by washing the filter with water.

RESULTS

Characterization of the MDMV-B Genome

Clones have been isolated and sequenced representing 8530 nucleotides of the MDMV-B genome. We have identified a single large open reading frame as would be expected of a virus belonging to the potyvirus family. We have identified regions of the polyprotein which would encode the coat protein (nucleotides 7308–8291 of SEQ ID No. 1), the putative RNA dependent RNA polymerase (RdRp) termed NIb (nucleotides 5745–7307 of SEQ ID No. 1), the NIa proteinase (nucleotides 4452–5744 of SEQ ID No. 1), the 6K protein (nucleotides 4293–4451 of SEQ ID No. 1), cylindrical inclusion protein (CIP) containing the helicase (nucleotides 2376–4292 of SEQ ID No. 1), P3 proteinase (nucleotides 1134–2375 of SEQ ID No. 1), and a portion of the helper component-P2 proteinase (HC-Pro)(nucleotides 3–1133 of SEQ ID No. 1). Identification was based on the location of putative cleavage sites and conserved motifs. The MDMV-B sequence of the CP region from our isolate was 99% identical to the previously sequenced MDMV-B CP and 78% identical to the MDMV-A CP. Further comparisons could not be made due to the lack of additional sequence to other MDMV strains. The sequence of MDMV-B was then compared to other potyviruses and was found to exhibit approximately 60% nucleotide sequence identity to other potyviruses. The level of identify varied little when sequences encoding the different proteins were used for the comparison.

$T_0$ Analysis

Eighteen lines (individual transformation events from selection and regeneration) were obtained from the experiments in this example. 17 of the 18 lines were positive by PCR for the selectable marker, and 14 for the gene of interest. All 14 events which were PCR positive for the NIa gene were also positive for expression in the Northern analysis. The predominate mRNA species was approximately 1300 nucleotides in length which would correspond to the predicted size of the transgene. A smaller species approximately 1000 nucleotides in length was also detected which most likely arose by processing. Differences in mRNA expression levels were seen between different events as well as between individual plants (siblings) from a given event. All PCR positive plants were used for seed production ($T_1$).

$T_1$ Analysis

Four plants from two different events were identified to be resistant to the virus inoculation as evidenced by the absence of visual symptoms. There was no correlation to Basta tolerance in this example. Northern analysis of the four plants showed no detectable NIa transcript in the four resistant plants, while an infected sibling plant from the same original ear ($T_0$) was shown to have high levels of viral RNA. The levels of MDMV-B in the infected sibling was similar to the levels seen in the control CG00526 plants.

The resistant plants were also evaluated for the presence of viral coat protein by ELISA. The four values obtained for each sample, duplicate samples from the inoculated leaf and non-inoculated leaf, were averaged and a comparison made against the infected and healthy controls. No detectable virus was present in the resistant transformed plant lines by ELISA at which the threshold of detection was approximately 2 ng of virus per sample. In contrast, the transformed siblings which exhibited symptoms contained levels of virus similar to that seen in the infected CG00526 control plants. These results show conclusive evidence that the four plants were immune to MDMV-B infection (i.e. not supporting virus replication). The resistance was durable in that the resistant plants withstood two inoculations with high MDMV-B inoculum concentrations. The inoculum concentrations used in these experiments typically result in symptoms within four days in susceptible plant lines. Yet, the resistant plants have not produced visible symptoms nor detectable virus six weeks following inoculation.

Various modifications of the invention described herein will become apparent to those skilled in the art. Such modifications are intended to fall within the scope of the appended claims.

We claim:

1. A chimeric gene comprising a promoter functional in plants operably linked to a coding sequence for a translationally altered RNA, wherein said translationally altered RNA comprises a messenger RNA sequence of a maize dwarf mosaic virus having a modification which renders said messenger RNA incapable of expressing a protein greater than twenty amino acids in length.

2. The chimeric gene of claim 1 wherein said maize dwarf mosaic virus is maize dwarf mosaic virus strain B.

3. The chimeric gene of claim 1 wherein said translationally altered RNA is capable of translating an attenuated peptide which corresponds to a portion of the peptide encoded by said messenger RNA sequence.

4. The chimeric gene of claim 3 wherein said attenuated peptide is less than 20 amino acids in length.

5. The chimeric gene of claim 1 wherein said translationally altered RNA is incapable of being translated.

6. The chimeric gene of claim 1 wherein said messenger RNA sequence does not include the translation initiation codon of said maize dwarf mosaic virus, strain B.

7. The chimeric gene of claim 1 wherein said messenger RNA sequence encodes a portion of a viral protein selected from the group consisting of a coat protein, a proteinase, a replicase, a helicase, a Vpg, a 6K protein and a helper component.

8. The chimeric gene of claim 1 wherein said modification comprises the addition of a premature stop codon into said messenger RNA sequence.

9. The chimeric gene of claim 8 wherein said messenger RNA sequence comprises nucleotides 4452 to 5744 of SEQ ID No. 1 and said modification comprises the substitution of a T for the A at position 4470 of SEQ ID No. 1.

10. The chimeric gene of claim 9 wherein said modification further comprises the insertion of an ATG codon immediately before the G at position 4452 of SEQ ID No. 1.

11. The gene of claim 1 wherein said promoter functional in plants is selected from the group consisting of a maize ubiquitin promoter, a maize actin promoter and a maize phosphoenolpyruvate carboxylase promoter.

12. A method for producing a monocotyledonous plant with an inheritable trait of resistance to infection by a maize dwarf mosaic virus comprising transforming said plant with a chimeric gene comprising a promoter functional in monocotyledonous plants operably linked to a coding sequence for a translationally altered RNA, wherein said translationally altered RNA comprises a messenger RNA sequence of said maize dwarf mosaic virus having a modification which renders said messenger RNA incapable of expressing a protein greater than twenty amino acids in length, wherein expression of said chimeric gene in said monocotyledonous plant inhibits infection by said maize dwarf mosaic virus.

13. A monocotyledonous plant comprising a chimeric gene comprising a promoter functional in monocotyledonous plants operably linked to a coding sequence for a translationally altered RNA, wherein said translationally altered RNA comprises a messenger RNA sequence of a maize dwarf mosaic virus having a modification which renders said messenger RNA incapable of expressing a protein greater than twenty amino acids in length.

14. The monocotyledonous plant of claim 13 wherein said monocotyledonous plant is selected from the group consisting of maize, sorghum and sugar cane.

15. The monocotyledonous plant of claim 14 wherein said monocotyledonous plant is maize.

* * * * *

```
                           SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
          (A) LENGTH: 8543 base pairs
          (B) TYPE: nucleic acid
          (C) STRANDEDNESS: single
          (D) TOPOLOGY: linear (ii) MOLECULE TYPE: RNA (genomic)

(iii) HYPOTHETICAL: NO (ix) FEATURE:
          (A) NAME/KEY: CDS
          (B) LOCATION: 3..8291
          (D) OTHER INFORMATION: /product= "polyprotein encoded by
                MDMV-B genome"

(ix) FEATURE:
          (A) NAME/KEY: 3'UTR
          (B) LOCATION: 8292..8530

(ix) FEATURE:
          (A) NAME/KEY: misc_RNA
          (B) LOCATION: 3..1133
          (D) OTHER INFORMATION: /product= "3-prime sequence for
                HC-Pro"

(ix) FEATURE:
          (A) NAME/KEY: misc_RNA
          (B) LOCATION: 1134..2375
          (D) OTHER INFORMATION: /product= "P3 proteinase"

(ix) FEATURE:
          (A) NAME/KEY: misc_RNA
          (B) LOCATION: 2376..4292
          (D) OTHER INFORMATION: /product= "cylindrical inclusion
                protein"

(ix) FEATURE:
          (A) NAME/KEY: misc_RNA
          (B) LOCATION: 4293..4451
          (D) OTHER INFORMATION: /product= "K2 (6kD protein)"

(ix) FEATURE:
          (A) NAME/KEY: misc_RNA
          (B) LOCATION: 4452..5744
          (D) OTHER INFORMATION: /product= "NIa proteinase"

(ix) FEATURE:
          (A) NAME/KEY: misc_RNA
          (B) LOCATION: 5745..7307
          (D) OTHER INFORMATION: /product= "NIb replicase"

(ix) FEATURE:
          (A) NAME/KEY: misc_RNA
          (B) LOCATION: 7308..8291
          (D) OTHER INFORMATION: /product= "coat protein"

(xi) SEQUENCE DESCRIPTION: SEQ ID NO:1:
```

-continued

| | |
|---|---|
| UC GAA GAG AAA CAA CGA GAG UAU CUU GCA AAG GAU CAA AAA CUA UCC<br>   Glu Glu Lys Gln Arg Glu Tyr Leu Ala Lys Asp Gln Lys Leu Ser<br>    1             5                 10                15 | 47 |
| AGA AUG AUA CAA UUU AUC AAA GAA AGG UGC AAU CCA AAA UUU UCG CAU<br>Arg Met Ile Gln Phe Ile Lys Glu Arg Cys Asn Pro Lys Phe Ser His<br>           20                25               30 | 95 |
| UUA CCA ACG CUA UGG CAA GUC GCG GAA ACA AUA GGG CAC UAU ACU GAU<br>Leu Pro Thr Leu Trp Gln Val Ala Glu Thr Ile Gly His Tyr Thr Asp<br>      35                 40               45 | 143 |
| AAC CAG UCA AAG CAA AUA AUG GAU GUU AGC GAA GCG CUC AUC AAA GUU<br>Asn Gln Ser Lys Gln Ile Met Asp Val Ser Glu Ala Leu Ile Lys Val<br>        50                55               60 | 191 |
| AAU ACU CUG ACU CCU GAU GAU GCU AUG AAA GCA AGC GCA GCG UUA CUU<br>Asn Thr Leu Thr Pro Asp Asp Ala Met Lys Ala Ser Ala Ala Leu Leu<br>     65              70               75 | 239 |
| GAA GUG UCG CGA UGG UAU AAG AAU CGU AAG GAG UCA CUC AAA ACU GAC<br>Glu Val Ser Arg Trp Tyr Lys Asn Arg Lys Glu Ser Leu Lys Thr Asp<br>80                85               90               95 | 287 |
| UCA UUG GAA UCU UUU AGA AAU AAA AUA UCA CCA AAG AGU ACA AUA AAU<br>Ser Leu Glu Ser Phe Arg Asn Lys Ile Ser Pro Lys Ser Thr Ile Asn<br>              100              105             110 | 335 |
| GCA GCU UUA AUG UGC GAU AAU CAA UUG GAU AAA AAU GCA AAU UUU GUA<br>Ala Ala Leu Met Cys Asp Asn Gln Leu Asp Lys Asn Ala Asn Phe Val<br>         115               120             125 | 383 |
| UGG GGU AAU AGG GAA UAC CAC GCC AAA CGA UUU UUC GCA AAC UAU UUU<br>Trp Gly Asn Arg Glu Tyr His Ala Lys Arg Phe Phe Ala Asn Tyr Phe<br>       130               135             140 | 431 |
| NAA GCA GUG GAU CCC ACA GAU GCA UAU GAA AAG CAC GUC ACA CGG UUC<br>Xaa Ala Val Asp Pro Thr Asp Ala Tyr Glu Lys His Val Thr Arg Phe<br>145                150              155 | 479 |
| AAC CCU AAU GGU CAA CGA AAG UUA UCA AUA GGA AAG UUA GUU AUC CCA<br>Asn Pro Asn Gly Gln Arg Lys Leu Ser Ile Gly Lys Leu Val Ile Pro<br>160                165              170             175 | 527 |
| CUA GAC UUU CAA AAG AUU AGA GAA UCA UUC GUU GGA CUC UCG AUA AAU<br>Leu Asp Phe Gln Lys Ile Arg Glu Ser Phe Val Gly Leu Ser Ile Asn<br>         180               185             190 | 575 |
| AGA CAA CCG CUG GAU AAA UGU UGU GUU AGC AAG AUC GAA GGA GGG UAU<br>Arg Gln Pro Leu Asp Lys Cys Cys Val Ser Lys Ile Glu Gly Gly Tyr<br>          195              200             205 | 623 |
| AUA UAC CCA UGU UGC UGC GUC ACA ACA GAA UUU GGU AAA CCA GCA UAC<br>Ile Tyr Pro Cys Cys Cys Val Thr Thr Glu Phe Gly Lys Pro Ala Tyr<br>       210               215             220 | 671 |
| UCU GAG AUA AUA CCU CCA ACG AAA GGG CAU AUA ACA AUA GGC AAU UCU<br>Ser Glu Ile Ile Pro Pro Thr Lys Gly His Ile Thr Ile Gly Asn Ser<br>225                230              235 | 719 |
| AUU GAU UCA AAG AUU GUG GAC UUG CCA AAU ACA ACA CCC AGC AUG<br>Ile Asp Ser Lys Ile Val Asp Leu Pro Asn Thr Thr Pro Ser Met<br>240                245              250             255 | 767 |
| UAC AUU GCU AAG GAU GGG UAU UGC UAC AUC AAC AUC UUU UUA GCA GCC<br>Tyr Ile Ala Lys Asp Gly Tyr Cys Tyr Ile Asn Ile Phe Leu Ala Ala<br>          260              265             270 | 815 |
| AUG AUC AAC GUU AAU GAA GAA UCU GCC AAG GAU UAU ACG AAA UUU UUG<br>Met Ile Asn Val Asn Glu Glu Ser Ala Lys Asp Tyr Thr Lys Phe Leu<br>         275               280             285 | 863 |
| AGG GAC GAA CUA GUU GAG CGU CUC GGA AAG UGG CCA AAG CUU AAA GAC<br>Arg Asp Glu Leu Val Glu Arg Leu Gly Lys Trp Pro Lys Leu Lys Asp<br>          290              295             300 | 911 |

-continued

| | |
|---|---|
| GUA GCA ACA GCG UGU UAU GCA UUA UCU GUA AUG UUU CCA GAA AUU AAG<br>Val Ala Thr Ala Cys Tyr Ala Leu Ser Val Met Phe Pro Glu Ile Lys<br>305                          310                        315 | 959 |
| AAU GCU GAG CUA CCU CCA AUU CUA GUU GAC CAU GAA AAU AAA UCA AUG<br>Asn Ala Glu Leu Pro Pro Ile Leu Val Asp His Glu Asn Lys Ser Met<br>320                        325                        330                   335 | 1007 |
| CAC GUA AUC GAU UCA UAU GGU UCA CUA AGC GUU GGA UUU CAC AUA UUA<br>His Val Ile Asp Ser Tyr Gly Ser Leu Ser Val Gly Phe His Ile Leu<br>                      340                        345                        350 | 1055 |
| AAA GCA AGC ACG AUU GGU CAA UUA AUC AAA UUU CAA UAU GAG UCU AUG<br>Lys Ala Ser Thr Ile Gly Gln Leu Ile Lys Phe Gln Tyr Glu Ser Met<br>                      355                        360                        365 | 1103 |
| GAU AGU GAA AUG CGC GAA UAC AUA GUA GGA GGA ACU CUC ACA CAA CAG<br>Asp Ser Glu Met Arg Glu Tyr Ile Val Gly Gly Thr Leu Thr Gln Gln<br>        370                        375                        380 | 1151 |
| ACA UUC AAC ACA CUU CUU AAG AUG CUU ACG AAA AAC AUG UUC AAA CCA<br>Thr Phe Asn Thr Leu Leu Lys Met Leu Thr Lys Asn Met Phe Lys Pro<br>385                          390                        395 | 1199 |
| GAG CGC AUC AAG CAG AUA AUU GAA GAG GAA CCU UUC UUA CUU AUG AUG<br>Glu Arg Ile Lys Gln Ile Ile Glu Glu Glu Pro Phe Leu Leu Met Met<br>400                          405                        410                   415 | 1247 |
| GCG AUU GCG UCU CCA ACG GUA UUA AUA GCA CUA UAU AAU AAU UGU UAU<br>Ala Ile Ala Ser Pro Thr Val Leu Ile Ala Leu Tyr Asn Asn Cys Tyr<br>                      420                        425                        430 | 1295 |
| AUU GAG CAA GCU AUG ACA UAC UGG AUC GUU AAG AAU CAA GGA GUU GCA<br>Ile Glu Gln Ala Met Thr Tyr Trp Ile Val Lys Asn Gln Gly Val Ala<br>                      435                        440                        445 | 1343 |
| GCC AUA UUC GCA CAA CUC GAA GCA UUA GCC AAG AAA ACA UCC CAG GCU<br>Ala Ile Phe Ala Gln Leu Glu Ala Leu Ala Lys Lys Thr Ser Gln Ala<br>        450                        455                        460 | 1391 |
| GAG CUA UUA GUU CUA CAA AUG CAG AUA CUU GAA AAA GCA UCU AAC CAA<br>Glu Leu Leu Val Leu Gln Met Gln Ile Leu Glu Lys Ala Ser Asn Gln<br>                      465                        470                        475 | 1439 |
| UUA AGA UUA GCA GUU UCA GGA CUU AGC CAU AUC GAC CCA GCA AAG CGA<br>Leu Arg Leu Ala Val Ser Gly Leu Ser His Ile Asp Pro Ala Lys Arg<br>480                          485                        490                   495 | 1487 |
| CUU UUG UGG UCA CAC CUU GAA GCG AUG UCA ACA CGA UCA GAA AUG AAC<br>Leu Leu Trp Ser His Leu Glu Ala Met Ser Thr Arg Ser Glu Met Asn<br>                      500                        505                        510 | 1535 |
| AAG GAG UUA AUA GCU GAG GGG UAU GCA CUA UAU GAC GAG CGC CUA UAC<br>Lys Glu Leu Ile Ala Glu Gly Tyr Ala Leu Tyr Asp Glu Arg Leu Tyr<br>                      515                        520                        525 | 1583 |
| ACC CUG AUG GAA AAA AGU UAC GUA GAU CAA UUA AAC CAA UCA UGG GCA<br>Thr Leu Met Glu Lys Ser Tyr Val Asp Gln Leu Asn Gln Ser Trp Ala<br>        530                        535                        540 | 1631 |
| GAA UUG UCA UAC UGU GGA AAA UUU UCA GCA AUA UGG CGU GUG UUC AGA<br>Glu Leu Ser Tyr Cys Gly Lys Phe Ser Ala Ile Trp Arg Val Phe Arg<br>545                          550                        555 | 1679 |
| GUC AGG AAG UAU UAC AAA CCG UCU UUA ACC GUG AGA AAA AGC GUA GAU<br>Val Arg Lys Tyr Tyr Lys Pro Ser Leu Thr Val Arg Lys Ser Val Asp<br>560                          565                        570                   575 | 1727 |
| UUA GGC GCU GUA UAC AAU AUA UCA GCU ACG CAU CUA AUA UCA GAU UUA<br>Leu Gly Ala Val Tyr Asn Ile Ser Ala Thr His Leu Ile Ser Asp Leu<br>                      580                        585                        590 | 1775 |
| GCG CGG AAA AGU CAA GAU CAA GUC AGC UCU AUU UUA ACC AAA CUC CGC<br>Ala Arg Lys Ser Gln Asp Gln Val Ser Ser Ile Leu Thr Lys Leu Arg<br>                      595                        600                        605 | 1823 |

-continued

| | |
|---|---|
| AAC GGU UUU UAU GAU AAA UUA GAG AAA GUU AGA AUA CGA ACU AUA AAA<br>Asn Gly Phe Tyr Asp Lys Leu Glu Lys Val Arg Ile Arg Thr Ile Lys<br>610                       615                  620 | 1871 |
| ACG GUU UAU UGG UUU AUA CCU GAU AUA UUU AGA CUC GUG CAC AUA UUC<br>Thr Val Tyr Trp Phe Ile Pro Asp Ile Phe Arg Leu Val His Ile Phe<br>625                       630                  635 | 1919 |
| AUA GUU UUG AGU UUA UUA ACU ACC AUC GCU AAC ACU AUC AUA GUA ACU<br>Ile Val Leu Ser Leu Leu Thr Thr Ile Ala Asn Thr Ile Ile Val Thr<br>640                       645                  650                  655 | 1967 |
| AUG AAU GAC UAC AAG AAA UUG AAG AAG CAA CAA AGA GAA GAC GAA UAU<br>Met Asn Asp Tyr Lys Lys Leu Lys Lys Gln Gln Arg Glu Asp Glu Tyr<br>                     660                  665                       670 | 2015 |
| GAA GCA GAA AUU AGC GAA GUU CGC AGA AUC CAU UCU ACC UUA AUG GAA<br>Glu Ala Glu Ile Ser Glu Val Arg Arg Ile His Ser Thr Leu Met Glu<br>             675                  680                  685 | 2063 |
| GAG CGG AAG GAC AAU CUG ACG UGU GAA CAA UUU AUU GAG UAU AUG CGU<br>Glu Arg Lys Asp Asn Leu Thr Cys Glu Gln Phe Ile Glu Tyr Met Arg<br>690                       695                  700 | 2111 |
| CMA AAU CAU CCA CGG CUA GUU GGA GNA ACA CUG GAC UUG ACU CAC ACA<br>Xaa Asn His Pro Arg Leu Val Gly Xaa Thr Leu Asp Leu Thr His Thr<br>705                       710                  715 | 2159 |
| GGU GUC AUA CAU GAA GGG AAA UCC AAU CUC GAA ACC AAU UUG GAA CAG<br>Gly Val Ile His Glu Gly Lys Ser Asn Leu Glu Thr Asn Leu Glu Gln<br>720                       725                  730                  735 | 2207 |
| UCA AUG GCA GUU GGA ACC UUG AUA ACA AUG AUA CUU GAU CCA CAG AAA<br>Ser Met Ala Val Gly Thr Leu Ile Thr Met Ile Leu Asp Pro Gln Lys<br>                     740                  745                     750 | 2255 |
| AGC GAU GCU GUC UAU AAG GUG UUG AAC AAA AUG CGG ACA GUA AUU AGU<br>Ser Asp Ala Val Tyr Lys Val Leu Asn Lys Met Arg Thr Val Ile Ser<br>             755                  760                  765 | 2303 |
| ACA AUU GAA CAA AAC GUC CCA UUC CCU UCA GUG AAU UUC UCC AAC AUC<br>Thr Ile Glu Gln Asn Val Pro Phe Pro Ser Val Asn Phe Ser Asn Ile<br>770                       775                  780 | 2351 |
| UUA ACA CCU CCA GUG GCA CAA CAG AGU GUA GAU GUU GAU GAG CCA UUA<br>Leu Thr Pro Pro Val Ala Gln Gln Ser Val Asp Val Asp Glu Pro Leu<br>785                       790                  795 | 2399 |
| ACA CUU AGC ACU GAU AAA AAU UUA ACA AUA GAC UUU GAC ACA AAU CAA<br>Thr Leu Ser Thr Asp Lys Asn Leu Thr Ile Asp Phe Asp Thr Asn Gln<br>800                       805                  810                  815 | 2447 |
| GAU UUA CCU GCC GAU ACA UUC AGU AAU GAU GUG ACA UUU GRA GAU UGG<br>Asp Leu Pro Ala Asp Thr Phe Ser Asn Asp Val Thr Phe Xaa Asp Trp<br>                     820                  825                  830 | 2495 |
| UGG UCA WMU CAA UUA AGC AAC AAC AGA ACA GUG SCA CAC UAC CGA CNU<br>Trp Ser Xaa Gln Leu Ser Asn Asn Arg Thr Val Xaa His Tyr Arg Xaa<br>             835                  840                  845 | 2543 |
| UGG GGG GAA AGU YCA UUG GAA UUC ACA CGA GAA AAC GCA GCC CAC ACG<br>Trp Gly Glu Ser Xaa Leu Glu Phe Thr Arg Glu Asn Ala Ala His Thr<br>850                       855                  860 | 2591 |
| AGC AUC GAA CUU GCA CAC UCA AAC AUU GAG AGG GAA UUC UUG CUU AGA<br>Ser Ile Glu Leu Ala His Ser Asn Ile Glu Arg Glu Phe Leu Leu Arg<br>865                       870                  875 | 2639 |
| GGA GCA GUC GGC UCG GGA AAA UCC ACU GGG UUA CCA UAC CAU CUU AGC<br>Gly Ala Val Gly Ser Gly Lys Ser Thr Gly Leu Pro Tyr His Leu Ser<br>880                       885                  890                  895 | 2687 |
| AUG CGC GGA AAA GUG CUG CUA CUA GAG CCU ACA AGA CCG CUA GCU GAG<br>Met Arg Gly Lys Val Leu Leu Leu Glu Pro Thr Arg Pro Leu Ala Glu<br>                     900                  905                  910 | 2735 |

```
AAC GUG UGU AGG CAA CUA CAA GGA CCG CCA UUU AAC GUA AGU CCA ACU     2783
Asn Val Cys Arg Gln Leu Gln Gly Pro Pro Phe Asn Val Ser Pro Thr
            915                 920                 925

CUU CAA AUG CGU GGA UUA AGU UCC UUU GGA UGC ACU CCA AUC ACA AUC     2831
Leu Gln Met Arg Gly Leu Ser Ser Phe Gly Cys Thr Pro Ile Thr Ile
        930                 935                 940

AUG ACA UCU GGU UUC GCA UUG CAC AUG UAC GCA AAU AAU CCA GAU AAA     2879
Met Thr Ser Gly Phe Ala Leu His Met Tyr Ala Asn Asn Pro Asp Lys
945                 950                 955

AUA UCU GAG UAC GAU UUC AUA AUC UUU GAU GAA UGU CAU AUA AUG GAA     2927
Ile Ser Glu Tyr Asp Phe Ile Ile Phe Asp Glu Cys His Ile Met Glu
960                 965                 970                 975

GCA CCA GCG AUG GCC UUU UAU UGU UUA CUC AAA GAA UAU GAA UAU CGA     2975
Ala Pro Ala Met Ala Phe Tyr Cys Leu Leu Lys Glu Tyr Glu Tyr Arg
                980                 985                 990

GGA AAA AUU AUC AAG GUA UCA GCU ACG CCU CCA GGA AGG GAG UGU GAA     3023
Gly Lys Ile Ile Lys Val Ser Ala Thr Pro Pro Gly Arg Glu Cys Glu
            995                 1000                1005

UUC ACA ACA CAA CAU CCA GUA GAC AUC CAU GUU UGU GAG AAU CUA ACU     3071
Phe Thr Thr Gln His Pro Val Asp Ile His Val Cys Glu Asn Leu Thr
        1010                1015                1020

CAG CAA CAG UUU GUU AUG GAA CUC GGG ACU GGU UCA ACC GCA GAU GCU     3119
Gln Gln Gln Phe Val Met Glu Leu Gly Thr Gly Ser Thr Ala Asp Ala
    1025                1030                1035

ACG AAG UAC GGA AAU AAU AUC UUA GUU UAU GUA GCA AGC UAU AAU GAC     3167
Thr Lys Tyr Gly Asn Asn Ile Leu Val Tyr Val Ala Ser Tyr Asn Asp
1040                1045                1050                1055

GUC GAU UCA UUG UCG CAA GCA CUA GUC GAA CUU AAA UUU UCC GUA AUC     3215
Val Asp Ser Leu Ser Gln Ala Leu Val Glu Leu Lys Phe Ser Val Ile
                1060                1065                1070

AAA GUG GAU GGC CGA ACA AUG AAA CAA AAC ACA ACA GGA AUC AUU ACA     3263
Lys Val Asp Gly Arg Thr Met Lys Gln Asn Thr Thr Gly Ile Ile Thr
            1075                1080                1085

AAC GGU ACC GCA CAA AAG AAG UGU UUU GUU GUC GCA ACG AAU AUA AUU     3311
Asn Gly Thr Ala Gln Lys Lys Cys Phe Val Val Ala Thr Asn Ile Ile
        1090                1095                1100

GAG AAU GGC GUC ACA CUA GAU AUU GAU GUU GGU GUC GAC UUC GGA CUU     3359
Glu Asn Gly Val Thr Leu Asp Ile Asp Val Gly Val Asp Phe Gly Leu
    1105                1110                1115

AAA GUC UCA GCU GAC UUG GAC GUU GAC AAC AGG GCG GUA UUG UAU AAA     3407
Lys Val Ser Ala Asp Leu Asp Val Asp Asn Arg Ala Val Leu Tyr Lys
1120                1125                1130                1135

CGC GUA AGU AUA UCA UAU GGU GAA CUC AUA CAA CGA UUG GGU CGU GUU     3455
Arg Val Ser Ile Ser Tyr Gly Glu Leu Ile Gln Arg Leu Gly Arg Val
                1140                1145                1150

GGC AGA AAU AAA CCU GGU ACA GUU AUU CGA AUC GGA AAA ACA AUG AAA     3503
Gly Arg Asn Lys Pro Gly Thr Val Ile Arg Ile Gly Lys Thr Met Lys
            1155                1160                1165

GGU UUG CAG GAA AUU CCA GCA AUG AUC GCA ACA GAG GCA GCC UUC AUG     3551
Gly Leu Gln Glu Ile Pro Ala Met Ile Ala Thr Glu Ala Ala Phe Met
        1170                1175                1180

UGU UUC GCU UAC GGU CUU AAA GUU AUC ACU CAU AAU GUU UCA ACG ACC     3599
Cys Phe Ala Tyr Gly Leu Lys Val Ile Thr His Asn Val Ser Thr Thr
    1185                1190                1195

CAU CUU GCA AAG UGC ACA GUU AAA CAA GCG AGA ACC AUG AUG CAA UUU     3647
His Leu Ala Lys Cys Thr Val Lys Gln Ala Arg Thr Met Met Gln Phe
1200                1205                1210                1215
```

-continued

```
GAA UUA UCA CCA UUU GUC AUG GCU GAG CUC GUU AAG UUU GAU GGU UCA      3695
Glu Leu Ser Pro Phe Val Met Ala Glu Leu Val Lys Phe Asp Gly Ser
        1220            1225            1230

AUG CAU CCA CAA AUA CAU GAG GCA CUA GUA AAA UAC AAA CUU AGA GAU      3743
Met His Pro Gln Ile His Glu Ala Leu Val Lys Tyr Lys Leu Arg Asp
            1235            1240            1245

UCU GUC AUA AUG CUC AGA CCG AAU GCA CUU CCA AGG GUC AAU UUA CAU      3791
Ser Val Ile Met Leu Arg Pro Asn Ala Leu Pro Arg Val Asn Leu His
        1250            1255            1260

AAU UGG CUU ACA GCC CGA GAU UAU AAU AGA AUA GGA UGU UCA UUA GAA      3839
Asn Trp Leu Thr Ala Arg Asp Tyr Asn Arg Ile Gly Cys Ser Leu Glu
        1265            1270            1275

CUC GAA GAC CAC GUC AAA AUU CCG UAC UAC AUU AGG GGA GUU CCU GAC      3887
Leu Glu Asp His Val Lys Ile Pro Tyr Tyr Ile Arg Gly Val Pro Asp
1280            1285            1290            1295

AAG UUG UAU GGA AAG CUA UAU GAU AUC UUA CAG GAU AGU CCA ACU          3935
Lys Leu Tyr Gly Lys Leu Tyr Asp Ile Ile Leu Gln Asp Ser Pro Thr
            1300            1305            1310

AGU UGC UAC AGU AGA CUA UCA AGU GCG UGU GCA GGU AAA GUA GCA UAU      3983
Ser Cys Tyr Ser Arg Leu Ser Ser Ala Cys Ala Gly Lys Val Ala Tyr
        1315            1320            1325

ACU CUG CGA ACU GAU CCA UUU UCA CUU CCA AGA ACA AUA GCA AUA AUU      4031
Thr Leu Arg Thr Asp Pro Phe Ser Leu Pro Arg Thr Ile Ala Ile Ile
        1330            1335            1340

AAU GCC UYA AUC ACG GAG GAG UAU GCG AAG AGA GAU CAC UAU CGU AAC      4079
Asn Ala Xaa Ile Thr Glu Glu Tyr Ala Lys Arg Asp His Tyr Arg Asn
        1345            1350            1355

AUG AUU YCA AAC CCA UCU UCA UCA CAC GCA UUC UCA CUC AAU GGG UUG      4127
Met Ile Xaa Asn Pro Ser Ser Ser His Ala Phe Ser Leu Asn Gly Leu
1360            1365            1370            1375

GUG UCU AUG AUC GCU ACU AGA UAU AUG AAA GAC CAC ACA AAG GAG AAU      4175
Val Ser Met Ile Ala Thr Arg Tyr Met Lys Asp His Thr Lys Glu Asn
            1380            1385            1390

AUU GAC AAA CUC AUC AGA GUG CGU GAU CAA UUA CUU GAG UUU CAA GGU      4223
Ile Asp Lys Leu Ile Arg Val Arg Asp Gln Leu Leu Glu Phe Gln Gly
        1395            1400            1405

ACU GGA AUG CAA UUU CAA GAU CCA UCA GAA CUC AUG GAA AUU GGG GCU      4271
Thr Gly Met Gln Phe Gln Asp Pro Ser Glu Leu Met Glu Ile Gly Ala
        1410            1415            1420

CUC AAC ACA GUU AUU CAC CAA GGA AUG GAC GCA AUU GCA GCU UGU AUU      4319
Leu Asn Thr Val Ile His Gln Gly Met Asp Ala Ile Ala Ala Cys Ile
        1425            1430            1435

GAG UUA CAA GGA CGA UGG AAU GCU UCA CUU AUA CAA CGC GAU CUC CUA      4367
Glu Leu Gln Gly Arg Trp Asn Ala Ser Leu Ile Gln Arg Asp Leu Leu
1440            1445            1450            1455

AUU GCA GGU GGA GUU UUU AUC GGA GGC AUU UUG AUG AUG UGG AGC CUA      4415
Ile Ala Gly Gly Val Phe Ile Gly Gly Ile Leu Met Met Trp Ser Leu
            1460            1465            1470

UUU ACU AAA UGG AGU AAC ACA AAU GUC UCA CAU CAG GGG AAG AAC AAA      4463
Phe Thr Lys Trp Ser Asn Thr Asn Val Ser His Gln Gly Lys Asn Lys
        1475            1480            1485

CGC AGU AGA CAA AAA CUU CGA UUC AAA GAA GCA AGA GAC AAC AAA UAU      4511
Arg Ser Arg Gln Lys Leu Arg Phe Lys Glu Ala Arg Asp Asn Lys Tyr
        1490            1495            1500

GCA UAU GAU GUC ACA GGA UCG GAA GAA UGC CUU GGC GAG AAU UUU GGA      4559
Ala Tyr Asp Val Thr Gly Ser Glu Glu Cys Leu Gly Glu Asn Phe Gly
        1505            1510            1515
```

-continued

| | |
|---|---|
| ACA GCC UAU ACA AAG AAA GGU AAA GGA AAA GGA ACU AAA GUU GGA CUC<br>Thr Ala Tyr Thr Lys Lys Gly Lys Gly Lys Gly Thr Lys Val Gly Leu<br>1520                         1525                     1530                     1535 | 4607 |
| GGU GUG AAG CAG CAU AAA UUC CAU AUG AUG UAC GGU UUC GAU CCC CAA<br>Gly Val Lys Gln His Lys Phe His Met Met Tyr Gly Phe Asp Pro Gln<br>                     1540                     1545                     1550 | 4655 |
| GAG UAC AAC CUA AUU CGG UUU GUC GAU CCA CUC ACG GGA GCA ACU CUU<br>Glu Tyr Asn Leu Ile Arg Phe Val Asp Pro Leu Thr Gly Ala Thr Leu<br>           1555                     1560                     1565 | 4703 |
| GAU GAA CAA AUC CAU GCC GAU AUA CGC UUA AUU CAA GAG CAC UUC GCU<br>Asp Glu Gln Ile His Ala Asp Ile Arg Leu Ile Gln Glu His Phe Ala<br>1570                         1575                     1580 | 4751 |
| GAA AUU CGU GAG GAG GCA GUG AUU AAU GAC ACA AUU GAA AGG CAG CAG<br>Glu Ile Arg Glu Glu Ala Val Ile Asn Asp Thr Ile Glu Arg Gln Gln<br>           1585                     1590                     1595 | 4799 |
| AUU UAC GGC AAU CCU GGA CUA CAA GCA UUU UUC AUA CAA AAU GGG UCA<br>Ile Tyr Gly Asn Pro Gly Leu Gln Ala Phe Phe Ile Gln Asn Gly Ser<br>1600                         1605                     1610                     1615 | 4847 |
| GCA AAC GCU CUG AGA GUU GAU UUA ACA CCA CAU UCA CCU ACA CGA GUU<br>Ala Asn Ala Leu Arg Val Asp Leu Thr Pro His Ser Pro Thr Arg Val<br>                     1620                     1625                     1630 | 4895 |
| GUC ACA GGU AAU AAC AUA GCA GGG UUC CCA GAA UAU GAA GGA ACA CUU<br>Val Thr Gly Asn Asn Ile Ala Gly Phe Pro Glu Tyr Glu Gly Thr Leu<br>                     1635                     1640                     1645 | 4943 |
| CGU CAG ACU GGA ACA GCU AUA ACU AUA CCC AUU GGU CAA GUC CCA AUC<br>Arg Gln Thr Gly Thr Ala Ile Thr Ile Pro Ile Gly Gln Val Pro Ile<br>1650                         1655                     1660 | 4991 |
| GCA AAU GAA GCA GGG GUU GCA CAC GAG UCA AAA UCC AUG AUG AAC GGG<br>Ala Asn Glu Ala Gly Val Ala His Glu Ser Lys Ser Met Met Asn Gly<br>1665                         1670                     1675 | 5039 |
| UUG GGU GAU UAC ACA CCA AUA UCG CAA CAA UUG UGU CUA GUA CAA AAU<br>Leu Gly Asp Tyr Thr Pro Ile Ser Gln Gln Leu Cys Leu Val Gln Asn<br>1680                         1685                     1690                     1695 | 5087 |
| GAC UCG GAU GGG GUA AAG CGG AAU GUA UUU UCU AUU GGA UAU GGC UCA<br>Asp Ser Asp Gly Val Lys Arg Asn Val Phe Ser Ile Gly Tyr Gly Ser<br>                     1700                     1705                     1710 | 5135 |
| UAU CUU AUU UCA CCA GCG CAC UUA UUC AAA UAC AAC AAU GGU GAA AUA<br>Tyr Leu Ile Ser Pro Ala His Leu Phe Lys Tyr Asn Asn Gly Glu Ile<br>                     1715                     1720                     1725 | 5183 |
| ACA AUU AGA UCA UCA AGA GGA UUG UAC AAA AUU CGU AAU UCU GUG GAU<br>Thr Ile Arg Ser Ser Arg Gly Leu Tyr Lys Ile Arg Asn Ser Val Asp<br>1730                         1735                     1740 | 5231 |
| UUA AAA UUA CAU CCA AUU GCA CAC AGA GAC AUG GUC AUA AUU CAA CUC<br>Leu Lys Leu His Pro Ile Ala His Arg Asp Met Val Ile Ile Gln Leu<br>1745                         1750                     1755 | 5279 |
| CCA AAG GAU UUC CCA CCG UUC CCA AUG CGC UUG AAA UUC GAA CAA CCA<br>Pro Lys Asp Phe Pro Pro Phe Pro Met Arg Leu Lys Phe Glu Gln Pro<br>1760                         1765                     1770                     1775 | 5327 |
| UCA CGA GAU AUG CGA GUC UGC CUA GUA GGA GUC AAC UUC CAA CAG AAU<br>Ser Arg Asp Met Arg Val Cys Leu Val Gly Val Asn Phe Gln Gln Asn<br>                     1780                     1785                     1790 | 5375 |
| UAU AGC ACU UGC AUC GUA UCA GAA AGU AGU GUG ACA GCA CCA AAA GGA<br>Tyr Ser Thr Cys Ile Val Ser Glu Ser Ser Val Thr Ala Pro Lys Gly<br>                     1795                     1800                     1805 | 5423 |
| AAU GGA GAC UUU UGG AAA CAU UGG AUA UCA ACA GUC GAC GGU CAA UGU<br>Asn Gly Asp Phe Trp Lys His Trp Ile Ser Thr Val Asp Gly Gln Cys<br>1810                         1815                     1820 | 5471 |

-continued

```
GGA CUA CCA UUG GUA GAU ACU AAG AGC AAA CAU AUU GUC GGA AUU CAU      5519
Gly Leu Pro Leu Val Asp Thr Lys Ser Lys His Ile Val Gly Ile His
    1825                1830                1835

AGU CUU GCA UCA ACA AGU GGA AAC ACU AAU UUC UUU GUC GCU GUG CCU      5567
Ser Leu Ala Ser Thr Ser Gly Asn Thr Asn Phe Phe Val Ala Val Pro
1840                1845                1850                1855

GAG AAC UUU AAU GAA UAC AUC AAU GGA CUC GUG CAA GCA AAU AAA UGG      5615
Glu Asn Phe Asn Glu Tyr Ile Asn Gly Leu Val Gln Ala Asn Lys Trp
            1860                1865                1870

GAA AAA GGA UGG CAC UAU AAU CCG AAU CUC AUA UCC UGG UGU GGA CUA      5663
Glu Lys Gly Trp His Tyr Asn Pro Asn Leu Ile Ser Trp Cys Gly Leu
        1875                1880                1885

AAU UUA GUU GAU UCA GCC CCA AAA GGU UUG UUU AAA ACG UCA AAA UUG      5711
Asn Leu Val Asp Ser Ala Pro Lys Gly Leu Phe Lys Thr Ser Lys Leu
    1890                1895                1900

GUA GAA GAC UUG GAC GCG AGC GUU GAA GAG CAA UGC AAG AUC ACC GAA      5759
Val Glu Asp Leu Asp Ala Ser Val Glu Glu Gln Cys Lys Ile Thr Glu
1905                1910                1915

ACA UGG CUC ACA GAG CAA UUA CAA GAU AAU UUA CAA GUG GUU GCG AAA      5807
Thr Trp Leu Thr Glu Gln Leu Gln Asp Asn Leu Gln Val Val Ala Lys
1920                1925                1930                1935

UGU CCA GGC CAA CUA GUU ACC AAG CAU GUU GUU AAG GGU CAA UGC CCA      5855
Cys Pro Gly Gln Leu Val Thr Lys His Val Val Lys Gly Gln Cys Pro
            1940                1945                1950

CAC UUU CAA UUG UAC UUA UCA ACA CAU GAC GAU GCU AAA GAA UAC UUC      5903
His Phe Gln Leu Tyr Leu Ser Thr His Asp Asp Ala Lys Glu Tyr Phe
        1955                1960                1965

GCA CCC AUG CUU GGA AAA UAC GAC AAG AGU AGG CUU AAC AGA GCA GCU      5951
Ala Pro Met Leu Gly Lys Tyr Asp Lys Ser Arg Leu Asn Arg Ala Ala
    1970                1975                1980

UUU AUC AAA GAC AUA UCA AAA UAU GCA AAA CCA AUU UAC AUU GGA GAA      5999
Phe Ile Lys Asp Ile Ser Lys Tyr Ala Lys Pro Ile Tyr Ile Gly Glu
1985                1990                1995

AUC GAG UAU GAU AUC UUU GAU AGA GCU GUA CAG CGG GUU GUC AAU AUU      6047
Ile Glu Tyr Asp Ile Phe Asp Arg Ala Val Gln Arg Val Val Asn Ile
2000                2005                2010                2015

CUC AAA AAU GUU GGA AUG CAA CAA UGC GUU UAU GUC ACA GAU GAA GAA      6095
Leu Lys Asn Val Gly Met Gln Gln Cys Val Tyr Val Thr Asp Glu Glu
            2020                2025                2030

GAA AUU UUC AGA UCA CUU AAC CUG AAC GCA GCU GUC GGA GCA UUG UAU      6143
Glu Ile Phe Arg Ser Leu Asn Leu Asn Ala Ala Val Gly Ala Leu Tyr
        2035                2040                2045

ACA GGA AAG AAG AAA AAU UAC UUU GAA AAU UUU UCA AGC GAA GAC AAA      6191
Thr Gly Lys Lys Lys Asn Tyr Phe Glu Asn Phe Ser Ser Glu Asp Lys
    2050                2055                2060

GAA GAA AUC GUG AUG AGA UCC UGU GAA CGU AUU UAC AAU GGS CAA CUU      6239
Glu Glu Ile Val Met Arg Ser Cys Glu Arg Ile Tyr Asn Xaa Gln Leu
2065                2070                2075

GGC GUA UGG AAU GGA UCG CUC AAA GCU GAG AUC AGA CCA AUA GAG AAA      6287
Gly Val Trp Asn Gly Ser Leu Lys Ala Glu Ile Arg Pro Ile Glu Lys
2080                2085                2090                2095

ACC AUG CUG AAU AAG ACU CGA ACC UUC ACA GCG GCC CCA UUA GAA ACU      6335
Thr Met Leu Asn Lys Thr Arg Thr Phe Thr Ala Ala Pro Leu Glu Thr
            2100                2105                2110

UUG CUC GGA GGA AAA GUG UGC GUG GAU GAU UUU AAU AAU CAA UUC UAU      6383
Leu Leu Gly Gly Lys Val Cys Val Asp Asp Phe Asn Asn Gln Phe Tyr
        2115                2120                2125
```

```
UCA CAU CAU UUA GAA GGU CCA UGG ACU GUU GGG AUA ACA AAA UUC UAU      6431
Ser His His Leu Glu Gly Pro Trp Thr Val Gly Ile Thr Lys Phe Tyr
    2130                2135                2140

GGA GGU UGG AAU CGC UUA CUG GAG AAG UUA CCA GAA GGA UGG GUU UAC      6479
Gly Gly Trp Asn Arg Leu Leu Glu Lys Leu Pro Glu Gly Trp Val Tyr
            2145                2150                2155

UGC GAU GCU GAC GGG UCU CAA UUU GAU AGU UCG UUA ACA CCA UAU CUC      6527
Cys Asp Ala Asp Gly Ser Gln Phe Asp Ser Ser Leu Thr Pro Tyr Leu
2160                2165                2170                2175

AUC AAU GCA GUA UUA AAU AUU CGA UUG CAA UUU AUG GAA GAU UGG GAU      6575
Ile Asn Ala Val Leu Asn Ile Arg Leu Gln Phe Met Glu Asp Trp Asp
        2180                2185                2190

AUA GGA GCG CAA AUG CUA AAG AAC CUG UAC ACU GAG AUU GUU UAC ACA      6623
Ile Gly Ala Gln Met Leu Lys Asn Leu Tyr Thr Glu Ile Val Tyr Thr
            2195                2200                2205

CCA AUC GCA ACG CCA GAC GGA UCA AUC GUG AAG AAA UUC AAA GGU AAC      6671
Pro Ile Ala Thr Pro Asp Gly Ser Ile Val Lys Lys Phe Lys Gly Asn
                2210                2215                2220

AAU AGC GGA CAA CCU UCU ACA GUA GUG GAC AAC ACA UUG AUG GUU AUA      6719
Asn Ser Gly Gln Pro Ser Thr Val Val Asp Asn Thr Leu Met Val Ile
    2225                2230                2235

AUA GCU UUC AAC UAU GCC AUG CUA UCA AGU GGU AUC AAA GAA GAA GAA      6767
Ile Ala Phe Asn Tyr Ala Met Leu Ser Ser Gly Ile Lys Glu Glu Glu
2240                2245                2250                2255

AUC GAU AAU UGC UGU AGA AUG UUC GCG AAU GGU GAU GAC UUA CUC CUA      6815
Ile Asp Asn Cys Cys Arg Met Phe Ala Asn Gly Asp Asp Leu Leu Leu
        2260                2265                2270

GCA GUG CAU CCU GAU UUU GAG UUC AUU UUA GAU GAA UUU CAA AAU CAC      6863
Ala Val His Pro Asp Phe Glu Phe Ile Leu Asp Glu Phe Gln Asn His
            2275                2280                2285

UUU GGG AAU CUU GGG CUG AAC UUC GAA UUU ACA UCA CGA ACA CGA GAU      6911
Phe Gly Asn Leu Gly Leu Asn Phe Glu Phe Thr Ser Arg Thr Arg Asp
                2290                2295                2300

AAA UCC GAA CUG UGG UUC AUG UCC ACA AGA GGC AUC AAG UAU GAA GGA      6959
Lys Ser Glu Leu Trp Phe Met Ser Thr Arg Gly Ile Lys Tyr Glu Gly
    2305                2310                2315

AUU UAC AUA CCA AAG CUU GAG AAA GAA AGA AUA GUC GCC AUA CUU GAA      7007
Ile Tyr Ile Pro Lys Leu Glu Lys Glu Arg Ile Val Ala Ile Leu Glu
2320                2325                2330                2335

UGG GAU CGA UCA AAC UUG CCU GAA CAU AGG UUG GAA GCU AUA UGU GCA      7055
Trp Asp Arg Ser Asn Leu Pro Glu His Arg Leu Glu Ala Ile Cys Ala
        2340                2345                2350

GCG AUG GUU GAG GCC UGG GGA UAU UCC GAU CUC GUU CAU GAA AUA CGA      7103
Ala Met Val Glu Ala Trp Gly Tyr Ser Asp Leu Val His Glu Ile Arg
            2355                2360                2365

AAG UUC UAU GCG UGG CUU UUG GAA AUG CAA CCU UUU GCA AAU CUC GCA      7151
Lys Phe Tyr Ala Trp Leu Leu Glu Met Gln Pro Phe Ala Asn Leu Ala
                2370                2375                2380

AAA NAA GGG UUG GCC CCA UAC AUU GCC GAG ACA GCA CUC CGC AAU CUC      7199
Lys Xaa Gly Leu Ala Pro Tyr Ile Ala Glu Thr Ala Leu Arg Asn Leu
    2385                2390                2395

UAU CUU GGA ACG GGU AUC AAA GAG GAA GAA AUU GAA AAA UAU CUU AAA      7247
Tyr Leu Gly Thr Gly Ile Lys Glu Glu Glu Ile Glu Lys Tyr Leu Lys
2400                2405                2410                2415

CAA UUC AUU AAG GAU CUU CCC GGA UAC AUA GAA GAU UAC AAU GAA GAU      7295
Gln Phe Ile Lys Asp Leu Pro Gly Tyr Ile Glu Asp Tyr Asn Glu Asp
        2420                2425                2430
```

| | | |
|---|---|---|
| GUA UUC CAU CAG UCG GGA ACU GUU GAU GCG GGU GCA CAA GGC GGC AGU | 7343 | |
| Val Phe His Gln Ser Gly Thr Val Asp Ala Gly Ala Gln Gly Gly Ser | | |
|            2435                  2440                  2445 | | |
| GGA AGC CAA GGG ACA ACA CCA CCA GCA ACA GGU AGU GGA GCA AAA CCA | 7391 | |
| Gly Ser Gln Gly Thr Thr Pro Pro Ala Thr Gly Ser Gly Ala Lys Pro | | |
|         2450                  2455                  2460 | | |
| GCC ACC UCA GGG GCA GGA UCU GGU AGU GAC ACA GGA GCU GGA ACU GGU | 7439 | |
| Ala Thr Ser Gly Ala Gly Ser Gly Ser Asp Thr Gly Ala Gly Thr Gly | | |
|         2465                  2470                  2475 | | |
| GUA ACU GGA AGU CAA GCA AGG ACU GGC AGU GGC ACU GGG ACG GGA UCU | 7487 | |
| Val Thr Gly Ser Gln Ala Arg Thr Gly Ser Gly Thr Gly Thr Gly Ser | | |
| 2480                  2485                  2490                  2495 | | |
| GGA GCA ACC GGA GGC CAA UCA GGA UCU GGA AGU GGC ACU GAA CAG GUU | 7535 | |
| Gly Ala Thr Gly Gly Gln Ser Gly Ser Gly Ser Gly Thr Glu Gln Val | | |
|                 2500                  2505                  2510 | | |
| AAC ACG GGU UCA GCA GGA ACU AAU GCA ACU GGA GGC CAA AGA GAU AGG | 7583 | |
| Asn Thr Gly Ser Ala Gly Thr Asn Ala Thr Gly Gly Gln Arg Asp Arg | | |
|                 2515                  2520                  2525 | | |
| GAU GUG GAU GCA GGC UCA ACA GGA AAA AUU UCU GUA CCA AAG CUC AAG | 7631 | |
| Asp Val Asp Ala Gly Ser Thr Gly Lys Ile Ser Val Pro Lys Leu Lys | | |
|         2530                  2535                  2540 | | |
| GCC AUG UCA AAG AAA AUG CGC UUA CCU AAA GCA AAA GGA AAA GAU GUG | 7679 | |
| Ala Met Ser Lys Lys Met Arg Leu Pro Lys Ala Lys Gly Lys Asp Val | | |
|         2545                  2550                  2555 | | |
| CUA CAU UUG GAU UUU CUA UUG ACA UAC AAA CCA CAA CAA CAA GAC AUA | 7727 | |
| Leu His Leu Asp Phe Leu Leu Thr Tyr Lys Pro Gln Gln Gln Asp Ile | | |
| 2560                  2565                  2570                  2575 | | |
| UCA AAC ACU AGA GCA ACC AAG GAA GAG UUU GAU AGA UGG UAU GAU GCC | 7775 | |
| Ser Asn Thr Arg Ala Thr Lys Glu Glu Phe Asp Arg Trp Tyr Asp Ala | | |
|                 2580                  2585                  2590 | | |
| AUA AAG AAG GAA UAC GAA AUU GAU GAC ACA CAA AUG ACA GUU GUC AUG | 7823 | |
| Ile Lys Lys Glu Tyr Glu Ile Asp Asp Thr Gln Met Thr Val Val Met | | |
|                 2595                  2600                  2605 | | |
| AGU GGC CUU AUG GUA UGG UGC AUC GAA AAU GGU UGC UCA CCA AAC AUA | 7871 | |
| Ser Gly Leu Met Val Trp Cys Ile Glu Asn Gly Cys Ser Pro Asn Ile | | |
|         2610                  2615                  2620 | | |
| AAC GGA AAU UGG ACA AUG AUG GAU AAA GAU GAA CAA AGG GUC UUC CCA | 7919 | |
| Asn Gly Asn Trp Thr Met Met Asp Lys Asp Glu Gln Arg Val Phe Pro | | |
|         2625                  2630                  2635 | | |
| CUC AAA CCG GUC AUU GAG AAU GCA UCU CCA ACU UUC CGA CAA AUU AUG | 7967 | |
| Leu Lys Pro Val Ile Glu Asn Ala Ser Pro Thr Phe Arg Gln Ile Met | | |
| 2640                  2645                  2650                  2655 | | |
| CAU CAU UUC AGU GAU GCA GCU GAA GCG UAC AUA GAG UAC AGA AAC UCU | 8015 | |
| His His Phe Ser Asp Ala Ala Glu Ala Tyr Ile Glu Tyr Arg Asn Ser | | |
|                 2660                  2665                  2670 | | |
| ACU GAG CGA UAU AUG CCA AGA UAC GGA CUU CAG CGC AAU CUC ACC GAC | 8063 | |
| Thr Glu Arg Tyr Met Pro Arg Tyr Gly Leu Gln Arg Asn Leu Thr Asp | | |
|                 2675                  2680                  2685 | | |
| UAU AGC UUA GCA CGG UAU GCA UUU GAU UUC UAU GAA AUG ACU UCA CGC | 8111 | |
| Tyr Ser Leu Ala Arg Tyr Ala Phe Asp Phe Tyr Glu Met Thr Ser Arg | | |
|         2690                  2695                  2700 | | |
| ACA CCU GCU AGA GCU AAA GAA GCC CAC AUG CAG AUG AAA GCC GCA GCA | 8159 | |
| Thr Pro Ala Arg Ala Lys Glu Ala His Met Gln Met Lys Ala Ala Ala | | |
|         2705                  2710                  2715 | | |
| GUU CGU GGU UCA AAC ACA CGA CUG UUC GGU UUG GAU GGA AAU GUC GGC | 8207 | |
| Val Arg Gly Ser Asn Thr Arg Leu Phe Gly Leu Asp Gly Asn Val Gly | | |
| 2720                  2725                  2730                  2735 | | |

-continued

```
GAG ACU CAG GAG AAU ACA GAG AGA CAC ACA GCU GGC GAU GUU AGU CGC        8255
Glu Thr Gln Glu Asn Thr Glu Arg His Thr Ala Gly Asp Val Ser Arg
                2740                2745                2750

AAC AUG CAC UCU CUG UUG GGA GUG CAG CAA CAC CAC UAGUCUCCUG              8301
Asn Met His Ser Leu Leu Gly Val Gln Gln His His
            2755                2760

GAAACCCUGU UUGCAGUACC AAUAAUAUGU ACUAAUAUAU AGUAUUUUAG UGAGGUUUUA      8361

CCUCGUCUUU ACUGUUUUAU UACGUAUGUA UUUAAAGCGU GAACCAGUCU GCAACAUACA      8421

GGGUUGGACC CAGUGUGUUC UGGUGUAGCG UGUACUAGCG UCGAGCCAUG AGAUGGACUG      8481

CACUGGGUGU GGUUUUGCCA CUUGUGUUGC GAGUCUCCUG GUAAGAGACA AAAAAAAAAA      8541

AA                                                                     8543
```

(2) INFORMATION FOR SEQ ID NO:2:

(i) SEQUENCE CHARACTERISTICS:
        (A) LENGTH: 2763 amino acids
        (B) TYPE: amino acid
        (D) TOPOLOGY: linear (ii) MOLECULE TYPE: protein (xi) SEQUENCE DESCRIPTION: SEQ ID NO:2:

```
Glu Glu Lys Gln Arg Glu Tyr Leu Ala Lys Asp Gln Lys Leu Ser Arg
 1               5                  10                  15

Met Ile Gln Phe Ile Lys Glu Arg Cys Asn Pro Lys Phe Ser His Leu
                20                  25                  30

Pro Thr Leu Trp Gln Val Ala Glu Thr Ile Gly His Tyr Thr Asp Asn
            35                  40                  45

Gln Ser Lys Gln Ile Met Asp Val Ser Glu Ala Leu Ile Lys Val Asn
     50                  55                  60

Thr Leu Thr Pro Asp Asp Ala Met Lys Ala Ser Ala Leu Leu Glu
 65                  70                  75                  80

Val Ser Arg Trp Tyr Lys Asn Arg Lys Glu Ser Leu Lys Thr Asp Ser
                85                  90                  95

Leu Glu Ser Phe Arg Asn Lys Ile Ser Pro Lys Ser Thr Ile Asn Ala
                100                 105                 110

Ala Leu Met Cys Asp Asn Gln Leu Asp Lys Asn Ala Asn Phe Val Trp
            115                 120                 125

Gly Asn Arg Glu Tyr His Ala Lys Arg Phe Phe Ala Asn Tyr Phe Xaa
     130                 135                 140

Ala Val Asp Pro Thr Asp Ala Tyr Glu Lys His Val Thr Arg Phe Asn
145                 150                 155                 160

Pro Asn Gly Gln Arg Lys Leu Ser Ile Gly Lys Leu Val Ile Pro Leu
                165                 170                 175

Asp Phe Gln Lys Ile Arg Glu Ser Phe Val Gly Leu Ser Ile Asn Arg
                180                 185                 190

Gln Pro Leu Asp Lys Cys Cys Val Ser Lys Ile Glu Gly Gly Tyr Ile
            195                 200                 205

Tyr Pro Cys Cys Cys Val Thr Thr Glu Phe Gly Lys Pro Ala Tyr Ser
     210                 215                 220

Glu Ile Ile Pro Pro Thr Lys Gly His Ile Thr Ile Gly Asn Ser Ile
225                 230                 235                 240

Asp Ser Lys Ile Val Asp Leu Pro Asn Thr Thr Pro Pro Ser Met Tyr
                245                 250                 255
```

-continued

```
Ile Ala Lys Asp Gly Tyr Cys Tyr Ile Asn Ile Phe Leu Ala Ala Met
            260                 265                 270

Ile Asn Val Asn Glu Glu Ser Ala Lys Asp Tyr Thr Lys Phe Leu Arg
            275                 280                 285

Asp Glu Leu Val Glu Arg Leu Gly Lys Trp Pro Lys Leu Lys Asp Val
            290                 295                 300

Ala Thr Ala Cys Tyr Ala Leu Ser Val Met Phe Pro Glu Ile Lys Asn
305                 310                 315                 320

Ala Glu Leu Pro Pro Ile Leu Val Asp His Glu Asn Lys Ser Met His
                325                 330                 335

Val Ile Asp Ser Tyr Gly Ser Leu Ser Val Gly Phe His Ile Leu Lys
                340                 345                 350

Ala Ser Thr Ile Gly Gln Leu Ile Lys Phe Gln Tyr Glu Ser Met Asp
                355                 360                 365

Ser Glu Met Arg Glu Tyr Ile Val Gly Gly Thr Leu Thr Gln Gln Thr
            370                 375                 380

Phe Asn Thr Leu Leu Lys Met Leu Thr Lys Asn Met Phe Lys Pro Glu
385                 390                 395                 400

Arg Ile Lys Gln Ile Ile Glu Glu Pro Phe Leu Leu Met Met Ala
                405                 410                 415

Ile Ala Ser Pro Thr Val Leu Ile Ala Leu Tyr Asn Asn Cys Tyr Ile
                420                 425                 430

Glu Gln Ala Met Thr Tyr Trp Ile Val Lys Asn Gln Gly Val Ala Ala
            435                 440                 445

Ile Phe Ala Gln Leu Glu Ala Leu Ala Lys Lys Thr Ser Gln Ala Glu
        450                 455                 460

Leu Leu Val Leu Gln Met Gln Ile Leu Glu Lys Ala Ser Asn Gln Leu
465                 470                 475                 480

Arg Leu Ala Val Ser Gly Leu Ser His Ile Asp Pro Ala Lys Arg Leu
                485                 490                 495

Leu Trp Ser His Leu Glu Ala Met Ser Thr Arg Ser Glu Met Asn Lys
                500                 505                 510

Glu Leu Ile Ala Glu Gly Tyr Ala Leu Tyr Asp Glu Arg Leu Tyr Thr
            515                 520                 525

Leu Met Glu Lys Ser Tyr Val Asp Gln Leu Asn Gln Ser Trp Ala Glu
            530                 535                 540

Leu Ser Tyr Cys Gly Lys Phe Ser Ala Ile Trp Arg Val Phe Arg Val
545                 550                 555                 560

Arg Lys Tyr Tyr Lys Pro Ser Leu Thr Val Arg Lys Ser Val Asp Leu
                565                 570                 575

Gly Ala Val Tyr Asn Ile Ser Ala Thr His Leu Ile Ser Asp Leu Ala
                580                 585                 590

Arg Lys Ser Gln Asp Gln Val Ser Ser Ile Leu Thr Lys Leu Arg Asn
            595                 600                 605

Gly Phe Tyr Asp Lys Leu Glu Lys Val Arg Ile Arg Thr Ile Lys Thr
            610                 615                 620

Val Tyr Trp Phe Ile Pro Asp Ile Phe Arg Leu Val His Ile Phe Ile
625                 630                 635                 640

Val Leu Ser Leu Leu Thr Thr Ile Ala Asn Thr Ile Ile Val Thr Met
                645                 650                 655

Asn Asp Tyr Lys Lys Leu Lys Lys Gln Gln Arg Glu Asp Glu Tyr Glu
                660                 665                 670
```

```
Ala Glu Ile Ser Glu Val Arg Arg Ile His Ser Thr Leu Met Glu Glu
            675                 680                 685

Arg Lys Asp Asn Leu Thr Cys Glu Gln Phe Ile Glu Tyr Met Arg Xaa
        690                 695                 700

Asn His Pro Arg Leu Val Gly Xaa Thr Leu Asp Leu Thr His Thr Gly
705                 710                 715                 720

Val Ile His Glu Gly Lys Ser Asn Leu Glu Thr Asn Leu Glu Gln Ser
                725                 730                 735

Met Ala Val Gly Thr Leu Ile Thr Met Ile Leu Asp Pro Gln Lys Ser
            740                 745                 750

Asp Ala Val Tyr Lys Val Leu Asn Lys Met Arg Thr Val Ile Ser Thr
        755                 760                 765

Ile Glu Gln Asn Val Pro Phe Pro Ser Val Asn Phe Ser Asn Ile Leu
    770                 775                 780

Thr Pro Pro Val Ala Gln Gln Ser Val Asp Val Asp Glu Pro Leu Thr
785                 790                 795                 800

Leu Ser Thr Asp Lys Asn Leu Thr Ile Asp Phe Asp Thr Asn Gln Asp
                805                 810                 815

Leu Pro Ala Asp Thr Phe Ser Asn Asp Val Thr Phe Xaa Asp Trp Trp
            820                 825                 830

Ser Xaa Gln Leu Ser Asn Asn Arg Thr Val Xaa His Tyr Arg Xaa Trp
        835                 840                 845

Gly Glu Ser Xaa Leu Glu Phe Thr Arg Glu Asn Ala Ala His Thr Ser
850                 855                 860

Ile Glu Leu Ala His Ser Asn Ile Glu Arg Glu Phe Leu Leu Arg Gly
865                 870                 875                 880

Ala Val Gly Ser Gly Lys Ser Thr Gly Leu Pro Tyr His Leu Ser Met
                885                 890                 895

Arg Gly Lys Val Leu Leu Leu Glu Pro Thr Arg Pro Leu Ala Glu Asn
            900                 905                 910

Val Cys Arg Gln Leu Gln Gly Pro Pro Phe Asn Val Ser Pro Thr Leu
        915                 920                 925

Gln Met Arg Gly Leu Ser Ser Phe Gly Cys Thr Pro Ile Thr Ile Met
    930                 935                 940

Thr Ser Gly Phe Ala Leu His Met Tyr Ala Asn Asn Pro Asp Lys Ile
945                 950                 955                 960

Ser Glu Tyr Asp Phe Ile Ile Phe Asp Glu Cys His Ile Met Glu Ala
                965                 970                 975

Pro Ala Met Ala Phe Tyr Cys Leu Leu Lys Glu Tyr Glu Tyr Arg Gly
            980                 985                 990

Lys Ile Ile Lys Val Ser Ala Thr Pro Pro Gly Arg Glu Cys Glu Phe
        995                 1000                1005

Thr Thr Gln His Pro Val Asp Ile His Val Cys Glu Asn Leu Thr Gln
    1010                1015                1020

Gln Gln Phe Val Met Glu Leu Gly Thr Gly Ser Thr Ala Asp Ala Thr
1025                1030                1035                1040

Lys Tyr Gly Asn Asn Ile Leu Val Tyr Val Ala Ser Tyr Asn Asp Val
                1045                1050                1055

Asp Ser Leu Ser Gln Ala Leu Val Glu Leu Lys Phe Ser Val Ile Lys
            1060                1065                1070

Val Asp Gly Arg Thr Met Lys Gln Asn Thr Thr Gly Ile Ile Thr Asn
        1075                1080                1085
```

```
Gly Thr Ala Gln Lys Lys Cys Phe Val Val Ala Thr Asn Ile Ile Glu
    1090                1095                1100
Asn Gly Val Thr Leu Asp Ile Asp Val Gly Val Asp Phe Gly Leu Lys
1105                1110                1115                1120
Val Ser Ala Asp Leu Asp Val Asp Asn Arg Ala Val Leu Tyr Lys Arg
                1125                1130                1135
Val Ser Ile Ser Tyr Gly Glu Leu Ile Gln Arg Leu Gly Arg Val Gly
            1140                1145                1150
Arg Asn Lys Pro Gly Thr Val Arg Ile Gly Lys Thr Met Lys Gly
        1155                1160                1165
Leu Gln Glu Ile Pro Ala Met Ile Ala Thr Glu Ala Ala Phe Met Cys
    1170                1175                1180
Phe Ala Tyr Gly Leu Lys Val Ile Thr His Asn Val Ser Thr Thr His
1185                1190                1195                1200
Leu Ala Lys Cys Thr Val Lys Gln Ala Arg Thr Met Met Gln Phe Glu
                1205                1210                1215
Leu Ser Pro Phe Val Met Ala Glu Leu Val Lys Phe Asp Gly Ser Met
            1220                1225                1230
His Pro Gln Ile His Glu Ala Leu Val Lys Tyr Lys Leu Arg Asp Ser
        1235                1240                1245
Val Ile Met Leu Arg Pro Asn Ala Leu Pro Arg Val Asn Leu His Asn
    1250                1255                1260
Trp Leu Thr Ala Arg Asp Tyr Asn Arg Ile Gly Cys Ser Leu Glu Leu
1265                1270                1275                1280
Glu Asp His Val Lys Ile Pro Tyr Tyr Ile Arg Gly Val Pro Asp Lys
                1285                1290                1295
Leu Tyr Gly Lys Leu Tyr Asp Ile Ile Leu Gln Asp Ser Pro Thr Ser
            1300                1305                1310
Cys Tyr Ser Arg Leu Ser Ser Ala Cys Ala Gly Lys Val Ala Tyr Thr
        1315                1320                1325
Leu Arg Thr Asp Pro Phe Ser Leu Pro Arg Thr Ile Ala Ile Ile Asn
    1330                1335                1340
Ala Xaa Ile Thr Glu Glu Tyr Ala Lys Arg Asp His Tyr Arg Asn Met
1345                1350                1355                1360
Ile Xaa Asn Pro Ser Ser Ser His Ala Phe Ser Leu Asn Gly Leu Val
                1365                1370                1375
Ser Met Ile Ala Thr Arg Tyr Met Lys Asp His Thr Lys Glu Asn Ile
            1380                1385                1390
Asp Lys Leu Ile Arg Val Arg Asp Gln Leu Leu Glu Phe Gln Gly Thr
        1395                1400                1405
Gly Met Gln Phe Gln Asp Pro Ser Glu Leu Met Glu Ile Gly Ala Leu
    1410                1415                1420
Asn Thr Val Ile His Gln Gly Met Asp Ala Ile Ala Ala Cys Ile Glu
1425                1430                1435                1440
Leu Gln Gly Arg Trp Asn Ala Ser Leu Ile Gln Arg Asp Leu Leu Ile
                1445                1450                1455
Ala Gly Gly Val Phe Ile Gly Gly Ile Leu Met Met Trp Ser Leu Phe
            1460                1465                1470
Thr Lys Trp Ser Asn Thr Asn Val Ser His Gln Gly Lys Asn Lys Arg
        1475                1480                1485
Ser Arg Gln Lys Leu Arg Phe Lys Glu Ala Arg Asp Asn Lys Tyr Ala
    1490                1495                1500
```

-continued

```
Tyr Asp Val Thr Gly Ser Glu Glu Cys Leu Gly Glu Asn Phe Gly Thr
1505                1510                1515                1520

Ala Tyr Thr Lys Lys Gly Lys Gly Lys Gly Thr Lys Val Gly Leu Gly
            1525                1530                1535

Val Lys Gln His Lys Phe His Met Met Tyr Gly Phe Asp Pro Gln Glu
            1540                1545                1550

Tyr Asn Leu Ile Arg Phe Val Asp Pro Leu Thr Gly Ala Thr Leu Asp
            1555                1560                1565

Glu Gln Ile His Ala Asp Ile Arg Leu Ile Gln Glu His Phe Ala Glu
            1570                1575                1580

Ile Arg Glu Glu Ala Val Ile Asn Asp Thr Ile Glu Arg Gln Gln Ile
1585                1590                1595                1600

Tyr Gly Asn Pro Gly Leu Gln Ala Phe Phe Ile Gln Asn Gly Ser Ala
            1605                1610                1615

Asn Ala Leu Arg Val Asp Leu Thr Pro His Ser Pro Thr Arg Val Val
            1620                1625                1630

Thr Gly Asn Asn Ile Ala Gly Phe Pro Glu Tyr Glu Gly Thr Leu Arg
            1635                1640                1645

Gln Thr Gly Thr Ala Ile Thr Ile Pro Ile Gly Gln Val Pro Ile Ala
1650                1655                1660

Asn Glu Ala Gly Val Ala His Glu Ser Lys Ser Met Met Asn Gly Leu
1665                1670                1675                1680

Gly Asp Tyr Thr Pro Ile Ser Gln Gln Leu Cys Leu Val Gln Asn Asp
            1685                1690                1695

Ser Asp Gly Val Lys Arg Asn Val Phe Ser Ile Gly Tyr Gly Ser Tyr
            1700                1705                1710

Leu Ile Ser Pro Ala His Leu Phe Lys Tyr Asn Asn Gly Glu Ile Thr
            1715                1720                1725

Ile Arg Ser Ser Arg Gly Leu Tyr Lys Ile Arg Asn Ser Val Asp Leu
            1730                1735                1740

Lys Leu His Pro Ile Ala His Arg Asp Met Val Ile Ile Gln Leu Pro
1745                1750                1755                1760

Lys Asp Phe Pro Pro Phe Pro Met Arg Leu Lys Phe Glu Gln Pro Ser
            1765                1770                1775

Arg Asp Met Arg Val Cys Leu Val Gly Val Asn Phe Gln Gln Asn Tyr
            1780                1785                1790

Ser Thr Cys Ile Val Ser Glu Ser Ser Val Thr Ala Pro Lys Gly Asn
            1795                1800                1805

Gly Asp Phe Trp Lys His Trp Ile Ser Thr Val Asp Gly Gln Cys Gly
            1810                1815                1820

Leu Pro Leu Val Asp Thr Lys Ser Lys His Ile Val Gly Ile His Ser
1825                1830                1835                1840

Leu Ala Ser Thr Ser Gly Asn Thr Asn Phe Phe Val Ala Val Pro Glu
            1845                1850                1855

Asn Phe Asn Glu Tyr Ile Asn Gly Leu Val Gln Ala Asn Lys Trp Glu
            1860                1865                1870

Lys Gly Trp His Tyr Asn Pro Asn Leu Ile Ser Trp Cys Gly Leu Asn
            1875                1880                1885

Leu Val Asp Ser Ala Pro Lys Gly Leu Phe Lys Thr Ser Lys Leu Val
            1890                1895                1900

Glu Asp Leu Asp Ala Ser Val Glu Glu Gln Cys Lys Ile Thr Glu Thr
1905                1910                1915                1920
```

-continued

Trp Leu Thr Glu Gln Leu Gln Asp Asn Leu Gln Val Val Ala Lys Cys
            1925                1930                1935

Pro Gly Gln Leu Val Thr Lys His Val Val Lys Gly Gln Cys Pro His
        1940                1945                1950

Phe Gln Leu Tyr Leu Ser Thr His Asp Asp Ala Lys Glu Tyr Phe Ala
        1955                1960                1965

Pro Met Leu Gly Lys Tyr Asp Lys Ser Arg Leu Asn Arg Ala Ala Phe
    1970                1975                1980

Ile Lys Asp Ile Ser Lys Tyr Ala Lys Pro Ile Tyr Ile Gly Glu Ile
1985                1990                1995                2000

Glu Tyr Asp Ile Phe Asp Arg Ala Val Gln Arg Val Val Asn Ile Leu
        2005                2010                2015

Lys Asn Val Gly Met Gln Gln Cys Val Tyr Val Thr Asp Glu Glu
        2020                2025                2030

Ile Phe Arg Ser Leu Asn Leu Asn Ala Ala Val Gly Ala Leu Tyr Thr
        2035                2040                2045

Gly Lys Lys Lys Asn Tyr Phe Glu Asn Phe Ser Ser Glu Asp Lys Glu
    2050                2055                2060

Glu Ile Val Met Arg Ser Cys Glu Arg Ile Tyr Asn Xaa Gln Leu Gly
2065                2070                2075                2080

Val Trp Asn Gly Ser Leu Lys Ala Glu Ile Arg Pro Ile Glu Lys Thr
        2085                2090                2095

Met Leu Asn Lys Thr Arg Thr Phe Thr Ala Ala Pro Leu Glu Thr Leu
    2100                2105                2110

Leu Gly Gly Lys Val Cys Val Asp Asp Phe Asn Asn Gln Phe Tyr Ser
    2115                2120                2125

His His Leu Glu Gly Pro Trp Thr Val Gly Ile Thr Lys Phe Tyr Gly
        2130                2135                2140

Gly Trp Asn Arg Leu Leu Glu Lys Leu Pro Glu Gly Trp Val Tyr Cys
2145                2150                2155                2160

Asp Ala Asp Gly Ser Gln Phe Asp Ser Ser Leu Thr Pro Tyr Leu Ile
        2165                2170                2175

Asn Ala Val Leu Asn Ile Arg Leu Gln Phe Met Glu Asp Trp Asp Ile
        2180                2185                2190

Gly Ala Gln Met Leu Lys Asn Leu Tyr Thr Glu Ile Val Tyr Thr Pro
    2195                2200                2205

Ile Ala Thr Pro Asp Gly Ser Ile Val Lys Lys Phe Lys Gly Asn Asn
        2210                2215                2220

Ser Gly Gln Pro Ser Thr Val Val Asp Asn Thr Leu Met Val Ile Ile
2225                2230                2235                2240

Ala Phe Asn Tyr Ala Met Leu Ser Ser Gly Ile Lys Glu Glu Ile
        2245                2250                2255

Asp Asn Cys Cys Arg Met Phe Ala Asn Gly Asp Asp Leu Leu Leu Ala
        2260                2265                2270

Val His Pro Asp Phe Glu Phe Ile Leu Asp Glu Phe Gln Asn His Phe
    2275                2280                2285

Gly Asn Leu Gly Leu Asn Phe Glu Phe Thr Ser Arg Thr Arg Asp Lys
    2290                2295                2300

Ser Glu Leu Trp Phe Met Ser Thr Arg Gly Ile Lys Tyr Glu Gly Ile
2305                2310                2315                2320

Tyr Ile Pro Lys Leu Glu Lys Glu Arg Ile Val Ala Ile Leu Glu Trp
        2325                2330                2335

-continued

Asp Arg Ser Asn Leu Pro Glu His Arg Leu Glu Ala Ile Cys Ala Ala
        2340            2345            2350

Met Val Glu Ala Trp Gly Tyr Ser Asp Leu Val His Glu Ile Arg Lys
        2355            2360            2365

Phe Tyr Ala Trp Leu Leu Glu Met Gln Pro Phe Ala Asn Leu Ala Lys
        2370            2375            2380

Xaa Gly Leu Ala Pro Tyr Ile Ala Glu Thr Ala Leu Arg Asn Leu Tyr
2385            2390            2395            2400

Leu Gly Thr Gly Ile Lys Glu Glu Ile Glu Lys Tyr Leu Lys Gln
        2405            2410            2415

Phe Ile Lys Asp Leu Pro Gly Tyr Ile Glu Asp Tyr Asn Glu Asp Val
        2420            2425            2430

Phe His Gln Ser Gly Thr Val Asp Ala Gly Ala Gln Gly Gly Ser Gly
        2435            2440            2445

Ser Gln Gly Thr Thr Pro Pro Ala Thr Gly Ser Gly Ala Lys Pro Ala
        2450            2455            2460

Thr Ser Gly Ala Gly Ser Gly Ser Asp Thr Gly Ala Gly Thr Gly Val
2465            2470            2475            2480

Thr Gly Ser Gln Ala Arg Thr Gly Ser Gly Thr Gly Thr Gly Ser Gly
        2485            2490            2495

Ala Thr Gly Gly Gln Ser Gly Ser Gly Ser Gly Thr Glu Gln Val Asn
        2500            2505            2510

Thr Gly Ser Ala Gly Thr Asn Ala Thr Gly Gly Gln Arg Asp Arg Asp
        2515            2520            2525

Val Asp Ala Gly Ser Thr Gly Lys Ile Ser Val Pro Lys Leu Lys Ala
        2530            2535            2540

Met Ser Lys Lys Met Arg Leu Pro Lys Ala Lys Gly Lys Asp Val Leu
2545            2550            2555            2560

His Leu Asp Phe Leu Leu Thr Tyr Lys Pro Gln Gln Gln Asp Ile Ser
        2565            2570            2575

Asn Thr Arg Ala Thr Lys Glu Gly Phe Asp Arg Trp Tyr Asp Ala Ile
        2580            2585            2590

Lys Lys Glu Tyr Glu Ile Asp Asp Thr Gln Met Thr Val Val Met Ser
        2595            2600            2605

Gly Leu Met Val Trp Cys Ile Glu Asn Gly Cys Ser Pro Asn Ile Asn
        2610            2615            2620

Gly Asn Trp Thr Met Met Asp Lys Asp Glu Gln Arg Val Phe Pro Leu
2625            2630            2635            2640

Lys Pro Val Ile Glu Asn Ala Ser Pro Thr Phe Arg Gln Ile Met His
        2645            2650            2655

His Phe Ser Asp Ala Ala Glu Ala Tyr Ile Glu Tyr Arg Asn Ser Thr
        2660            2665            2670

Glu Arg Tyr Met Pro Arg Tyr Gly Leu Gln Arg Asn Leu Thr Asp Tyr
        2675            2680            2685

Ser Leu Ala Arg Tyr Ala Phe Asp Phe Tyr Glu Met Thr Ser Arg Thr
        2690            2695            2700

Pro Ala Arg Ala Lys Glu Ala His Met Gln Met Lys Ala Ala Ala Val
2705            2710            2715            2720

Arg Gly Ser Asn Thr Arg Leu Phe Gly Leu Asp Gly Asn Val Gly Glu
        2725            2730            2735

```
          Thr Gln Glu Asn Thr Glu Arg His Thr Ala Gly Asp Val Ser Arg Asn
                  2740                2745                2750

Met His Ser Leu Leu Gly Val Gln Gln His His
               2755                2760

(2) INFORMATION FOR SEQ ID NO:3:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "first Adh internal control
               primer"

(iii) HYPOTHETICAL: NO (xi) SEQUENCE DESCRIPTION: SEQ ID NO:3:

TGCATGTCGG TTGTGTTGCA                                                    20

(2) INFORMATION FOR SEQ ID NO:4:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "second Adh internal control
               primer"

(iii) HYPOTHETICAL: NO (xi) SEQUENCE DESCRIPTION: SEQ ID NO:4:

CTCAGCAAGT ACCTAGACCA                                                    20

(2) INFORMATION FOR SEQ ID NO:5:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "first synthetic PAT gene
               primer"

(iii) HYPOTHETICAL: NO (xi) SEQUENCE DESCRIPTION: SEQ ID NO:5:

TGTCTCCGGA GAGGAGACC                                                     19

(2) INFORMATION FOR SEQ ID NO:6:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "second synthetic PAT gene
               primer"
```

-continued (iii) HYPOTHETICAL: NO (xi) SEQUENCE DESCRIPTION: SEQ ID NO:6:

CCAACATCAT GCCATCCACC                                                                20

(2) INFORMATION FOR SEQ ID NO:7:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "first NIa proteinase gene
         primer"

(iii) HYPOTHETICAL: NO (xi) SEQUENCE DESCRIPTION: SEQ ID NO:7:

GCGGGATCCA TGGGGAAGAA CAAACGCAGT TGA                                              33

(2) INFORMATION FOR SEQ ID NO:8:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "second NIa proteinase
         primer"

(iii) HYPOTHETICAL: NO (xi) SEQUENCE DESCRIPTION: SEQ ID NO:8:

GCGGAGCTCT TACTCTTCAA CGCTCGCGTC                                                  30